(12) United States Patent
Shay et al.

(10) Patent No.: US 6,992,482 B2
(45) Date of Patent: Jan. 31, 2006

(54) MAGNETIC FIELD SENSOR HAVING A SWITCHABLE DRIVE CURRENT SPATIAL DISTRIBUTION

(75) Inventors: Ian Shay, Cambridge, MA (US); Neil J. Goldfine, Newton, MA (US); Andrew P. Washabaugh, Chula Vista, CA (US); Darrell E. Schlicker, Watertown, MA (US)

(73) Assignee: Jentek Sensors, Inc., Waltham, MA (US)

(*) Notice: Subject to any disclaimer, the term of this patent is extended or adjusted under 35 U.S.C. 154(b) by 143 days.

(21) Appl. No.: 10/045,650

(22) Filed: Nov. 8, 2001

(65) Prior Publication Data

US 2002/0158626 A1 Oct. 31, 2002

Related U.S. Application Data

(60) Provisional application No. 60/284,972, filed on Apr. 19, 2001, provisional application No. 60/277,532, filed on Mar. 21, 2001, provisional application No. 60/275,754, filed on Mar. 14, 2001, provisional application No. 60/246,853, filed on Nov. 8, 2000.

(51) Int. Cl.
    *G01N 27/82* (2006.01)
    *G01R 33/12* (2006.01)
(52) U.S. Cl. .................. 324/235; 324/232; 324/248; 324/240
(58) Field of Classification Search ........ 324/232–243, 324/228, 260, 248
See application file for complete search history.

(56) References Cited

U.S. PATENT DOCUMENTS

| 5,015,951 | A | | 5/1991 | Melcher ..................... 324/232 |
| 5,498,958 | A | * | 3/1996 | Tu et al. ................ 324/207.16 |
| 5,554,933 | A | | 9/1996 | Logue ....................... 324/233 |
| 5,629,621 | A | | 5/1997 | Goldfine et al. ............ 324/239 |
| 5,793,206 | A | | 8/1998 | Goldfine et al. ............ 324/242 |
| 6,002,251 | A | | 12/1999 | Sun ........................... 324/240 |
| 6,037,768 | A | | 3/2000 | Moulder et al. ............ 324/225 |
| 6,144,206 | A | | 11/2000 | Goldfine et al. ............ 324/345 |
| 6,150,809 | A | | 11/2000 | Tiernan et al. ............. 324/238 |
| RE36,986 | E | | 12/2000 | Melcher ..................... 324/232 |
| 6,188,218 | B1 | | 2/2001 | Goldfine et al. ............ 324/243 |
| 6,362,625 | B1 | | 3/2002 | Wiegert .................... 324/329 |

* cited by examiner

*Primary Examiner*—Jay Patidar
(74) *Attorney, Agent, or Firm*—Hamilton, Brook, Smith & Reynolds, PC

(57) ABSTRACT

Magnetic field sensor probes are disclosed which comprise primary or drive windings having a plurality of current carrying segments. The relative magnitude and direction of current in each segment are adjusted so that the resulting interrogating magnetic field follows a desired spatial distribution. By changing the current in each segment, more than one spatial distribution for the magnetic field can be imposed within the same sensor footprint. Example envelopes for the current distributions approximate a sinusoid in Cartesian coordinates or a first-order Bessel function in polar coordinates. One or more sensing elements are used to determine the response of a test material to the magnetic field. These sense elements can be configured into linear or circumferential arrays.

20 Claims, 24 Drawing Sheets

MAGNETIC FIELD SENSOR HAVING A SWITCHABLE DRIVE CURRENT SPATIAL DISTRIBUTION

RELATED APPLICATION(S)

This application claims the benefit of U.S. Provisional Application No. 60/246,853, filed Nov. 8, 2000, U.S. Provisional Application No. 60/275,754 filed Mar. 14, 2001, U.S. Provisional Application No. 60/277,532 filed Mar. 21, 2001, and U.S. Provisional Application No. 60/284,972 filed Apr. 19, 2001. The entire teachings of the above applications are incorporated herein by reference.

BACKGROUND

The technical field of this invention is that of nondestructive materials characterization, particularly quantitative, model-based characterization of surface, near-surface, and bulk material condition for flat and curved parts or components using eddy-current sensors. Characterization of bulk material condition includes (1) measurement of changes in material state caused by fatigue damage, creep damage, thermal exposure, or plastic deformation; (2) assessment of residual stresses and applied loads; and (3) assessment of processing-related conditions, for example from shot peening, roll burnishing, thermal-spray coating, or heat treatment. It also includes measurements characterizing material, such as alloy type, and material states, such as porosity and temperature. Characterization of surface and near-surface conditions includes measurements of surface roughness, displacement or changes in relative position, coating thickness, and coating condition. Each of these also includes detection of electromagnetic property changes associated with single or multiple cracks. Spatially periodic field eddy-current sensors have been used to measure foil thickness, characterize coatings, and measure porosity, as well as to measure property profiles as a function of depth into a part, as disclosed in U.S. Pat. Nos. 5,015,951 and 5,453,689.

Conventional eddy-current sensing involves the excitation of a conducting winding, the primary, with an electric current source of prescribed frequency. This produces a time-varying magnetic field at the same frequency, which in turn is detected with a sensing winding, the secondary. The spatial distribution of the magnetic field and the field measured by the secondary is influenced by the proximity and physical properties (electrical conductivity and magnetic permeability) of nearby materials. When the sensor is intentionally placed in close proximity to a test material, the physical properties of the material can be deduced from measurements of the impedance between the primary and secondary windings. Traditionally, scanning of eddy-current sensors across the material surface is then used to detect flaws, such as cracks.

One of the difficulties encountered when performing material property measurements with traditional spatially periodic field and other eddy current sensors is the limited sensitivity to flaws or defects, such as cracks, voids, inclusion, and corrosion, hidden behind metal layers or deep within the test material. A limiting factor for these measurements is often the frequency range of operation for the sensing device as it affects both the depth of penetration of the magnetic field into the test material and the detectable signal level of the device. The depth of penetration of the magnetic field into a material is determined by the geometry of the drive winding and the skin depth for the magnetic field in the material. The geometry affects the dominant spatial wavelength for the decay of the field into the material. For measurement sensitivity to a hidden flaw, both the dominant spatial wavelength and the skin depth need to be comparable to, or larger than, the thickness of material between the flaw and the sensor. Since the skin depth varies inversely with the square root of the frequency, sensitivity to deep flaws requires low excitation frequencies. The excitation frequency also affects the output signal level, which is the induced voltage from a secondary coil or winding for a traditional eddy current sensor. This voltage is proportional to the rate of change of the magnetic flux through the coil, and hence the excitation frequency. Since the induced voltage decreases with frequency, the lowest detectable signal level determines the lowest frequency of operation for the sensor, which may not be low enough for the detection of a flaw, according to the skin depth.

In addition, new materials, manufacturing processes and structural designs, as well as new damage mechanisms, pose continual challenges to the state-of-the-art in non-destructive evaluation. In particular, thick sections and multi-layered structures create difficult to inspect areas in which corrosion or other damage can propagate undetected. Although X-ray and ultrasonics have become common for inspection of thick structures and components (lapjoints, friction stir welds, turbine engine disks, and structural castings) for defects and geometric features, these techniques are limited in their sensitivity and image resolution. More importantly, they provide little, if any, information on absolute material properties. There is a need for lower cost, higher speed, wide area scanning capabilities not only to image defects, hidden corrosion, and geometric features, but also to provide images of metallurgical properties and residual stresses (e.g., for ferrous alloys magnetic permeability varies directly with applied and residual stress).

Giant magnetoresistive (GMR) and magnetoresistive sensing elements have been used to address this issue. Goldfine et al., described the use of arrays of magnetoresistive sensors with meandering drive windings in U.S. Pat. No. 5,793,206 as an alternative to inductive coils. Wincheski et. al. at NASA (Wincheski, 2001) and Raymond Rempt of Boeing (Rempt, 2001) have used single sensing elements and arrays of GMR or magnetoresistive sensing elements to detect subsurface cracks or corrosion.

A GMR sensor offers substantial new capabilities at a very reasonable cost compared to competing technologies, such as SQUIDs. GMRs take advantage of the large magnetoresistive effect exhibited by certain metallic magnetic superlattices. Whereas normal magnetoresistive materials exhibit maximum changes in resistance on the order of 5% when exposed to magnetic fields, GMRs exhibit resistance changes of 20% or more. Giant magnetoresistance was first observed in Fe/Cr magnetic superlattices, where a drop of as much as 45% of the resistivity was measured at liquid helium temperature. At room temperature, the magnitude of the effect was reduced to about 12%. Other material systems have been tested since then, with the Co/Cu magnetic superlattice emerging as the system of choice in the development of practical sensors. It exhibits resistivity drops of up to 55% at liquid helium temperature and 40% at room temperature.

A quantitative physical model of the giant magnetoresistive effect, developed by R. Q. Hood and L. M. Falicov, concludes that a large difference in interface scattering for the different spins is needed to explain the observed large GMR values. The magnetic superlattices have alternating layers of nonferromagnetic and ferromagnetic metals. The thickness of the nonferromagnetic layers is chosen such that in the absence of applied external magnetic field, the moments of consecutive ferromagnetic layers align antiparallel to each other. This antiferromagnetic coupling between these layers has been ascribed to indirect exchange interactions through the nonferromagnetic layers. The presence of an external field acts to align the moments of the ferromagnetic layers, resulting in reduction of the electric resistivity.

The sensitivity of GMRs to magnetic field strength and direction, as opposed to the rate of change of magnetic field strength, suggests the feasibility of a deep penetration eddy current type sensor. Typical eddy current devices lose sensitivity at lower frequencies. In order to achieve deep penetration of eddy currents, however, the excitation frequency must be decreased in order to increase the skin depth. The lack of sensitivity of simple inductive coils at low frequencies limits the depth of sensitivity of typical eddy current sensors in aluminum, for example, to a few millimeters. Replacing inductive coils or sense elements with GMR sensing elements has the potential to increase the depth of sensitivity. The term depth of sensitivity, not penetration, is used because the sensing elements do not affect the magnetic field depth of penetration provided by the drive windings.

Some progress has been made in adapting GMR sensors to non-destructive testing applications. Wincheski and Namkung have integrated a GMR with a self nulling probe driver coil to produce the Very Low Frequency (VLF) Self Nulling Probe. They have operated this device at excitation frequencies down to 135 Hz and have used it to detect an EDM notch at a depth of up to 10 mm (Wincheski, 2001). However, the need still exists to improve measurement reliability and robustness with GMR and magnetoresistive sensing element for eddy current and also for DC measurements with current driven drive windings.

SUMMARY

Aspects of the inventions described herein relates to methods and apparatus for the nondestructive measurements of materials using sensors that apply electromagnetic fields to a test material and detect changes in the electromagnetic fields due to the proximity and properties of the test material. Novel drive winding patterns are described which promote accurate modeling, varying the depth of penetration into the test material, and a reduced sensitivity to undesired and unmodeled parasitic response. The use of alternative sensors, such as GMRs, in the sensing elements is also described for improved sensitivity to low frequency, even dc, excitations. Arrays of these sensing elements promote imaging of surface and volumetric material property variations.

In one embodiment of this invention, alternative sensing elements are used with drive winding patterns that impose a magnetic field distribution on the test material. These sensing elements, such as magnetoresistive, GMR, Hall Effect, and SQUIDs, permit lower frequency operation than inductive coils used in conventional eddy current sensors. DC excitations can also be used. In a preferred embodiment, a GMR sensor is used as the sensing element and biased to operate in a regime where the output voltage of the GMR sensor is linear with magnetic field intensity. In another preferred embodiment, the GMR sensor is encircled by a feedback coil that biases the sensor and maintains a constant magnetic flux density in the vicinity of the sensor. The feedback current to this coil is performed by an electronic circuit. This mode of operation provides a larger dynamic range than a GMR sensor by itself and its ability to measure magnetic fields is only limited by the amplitude of the current that the electronic circuit can drive through the feedback coil. In another embodiment, high frequency measurements outside the operating range of the feedback circuit can be performed by operating the GMR sensor open-loop, without feedback, or by measuring the response of the feedback coil directly as with a conventional eddy current sensor.

When used with a shaped field distribution from the drive winding, the response of the GMR sensors can be accurately modeled. In one embodiment, these models are used with measurements of the sensor response in air to calibrate the sensor so that absolute property measurements can be obtained from the inspection of the test material. In another embodiment, these models can be used with measurements of the sensor response on a reference material, again so that absolute property measurements can be obtained from the test material. Properties that can be measured include the electrical conductivity, magnetic permeability, layer thicknesses and spatial property profiles, and the lift-off or proximity of the sensor to the test material. Measurements of these material properties can also be correlated to other physical properties, such as residual and applied stresses in magnetizable materials or temperature profiles across a material, and the presence of flaws or material degradation, such as corrosion, crack initiation and growth, detection of inclusions, and porosity. In one embodiment, low frequency measurements of the magnetic permeability are combined with high frequency measurements to determine the electrical conductivity.

In another embodiment, the model is used to create databases of response and measurement grids so that table look-up algorithms can be used to determine property values. These grids can be used, for example, to determine the electrical conductivity and lift-off of a test material, the electrical conductivity and thickness of a material given the lift-off value, and the magnetic permeability of a test material and lift-off, given the thickness of the test material.

In an embodiment of this invention, the drive-winding geometry and pattern is designed to shape of the imposed magnetic field to provide sensors with a deep depth of sensitivity to the test material properties. Near the sensor surface the magnetic field, in the quasistatic limit, decays essentially exponentially, at a rate determined by its spatial wavelength and the skin depth in the medium. For a deep depth of sensitivity into the test material, it is generally desirable to maximize the energy in the dominant spatial mode for the sensor, which has the fundamental spatial wavelength. Drive winding designs that gradually taper the current densities to zero near the ends of the winding structure tend to have less energy in the higher order spatial modes than designs that have abrupt changes or discontinuities in the current density at the ends. In one embodiment, drive-winding designs that gradually reduce the current density to zero near the ends of the winding structure reduce sensitivity to the higher order spatial modes, which have shallower penetration depths. Alternatively, in another embodiment, drive-winding designs that have abrupt changes or discontinuities in the current density at the ends are suitable for simultaneous measurements of both deep and shallow penetration depths.

In another embodiment, drive winding geometry and pattern can be designed to minimize sensitivity to unmodeled effects distant from the test material. In general, unmodeled effects in a sensor response can be compensated by proper sensor calibrations as long as the unmodeled effects are constant, independent of time and experimental conditions. However, unmodeled effects that are not constant cannot be eliminated with sensor calibration which, in turn, leads to a lack of measurement reproducibility. One source of these unmodeled effects is the presence of magnetizable or conducting objects in the vicinity of the sensor, which may cause the sensor response to change with time as the objects are moved or when the sensor is moved to new locations or scanned across a material. A factor that affects the sensor sensitivity to these objects is the decay rate of the magnetic fields around the sensor. Far from the sensor the magnetic field decays at a rate determined by the lowest order multi-pole moment excited by the sensor. Conventional shaped waveform sensors have a dipole moment and a relatively slow field decay rate with distance. In one embodiment, the drive winding pattern is designed so the dipole moments of each individual loop in the drive winding cancel. This permits faster field decay rates and less sensitivity to the extraneous presence of magnetizable and conducting material.

In another embodiment, methods for providing more than one spatial wavelength of the magnetic field excitation are described. Since the depth of sensitivity of the sensor depends on the dominant imposed spatial wavelength, the use of more than one excitation wavelength will provide information about the test material property variation with depth. The use of more than one wavelength within the same footprint has the additional advantage that the lift-off (distance between sensor and material) will be the same for both modes of operation. This is particularly useful when there are more than two unknown parameters and measurements under two different applied magnetic field distributions are necessary to determine all unknowns uniquely.

The fundamental or dominant wavelength of the current excitation can be altered without changing the geometry of the sensor by changing the current distribution in the segments of the drive winding. In one embodiment, this is accomplished by supplying an independent current drive for each segment and changing the relative magnitudes of these drives to create the desired field distribution. For example, the current distribution in the segments may follow a sinusoidal envelope function in Cartesian coordinates (or Bessel function in cylindrical geometry) of the desired spatial wavelength. In another embodiment, a design that avoids the need for multiple drive circuits uses two or more independent winding circuits to create the drive winding segments. Switching the relative current directions between the winding circuits can then alter the distribution of currents in the winding segments and the fundamental spatial wavelength for the current excitation. As an example, consider a drive having two separate winding circuits. In some segments of the drive, the current through the windings from each circuit are in the same direction while in other segments the current through the windings are in the opposite direction. This creates one spatial distribution for the net current in the drive segments. When the current through one of the drive circuits is switched to the opposite polarity, the spatial distribution of the current in the drive segments is also altered.

These method for designing the drive winding structure for sensors that impose a shaped magnetic field distribution over a finite sensor footprint are applicable to non-periodic sensors or sensors with a small number of periods, typically one to four, that are not wide enough to be modeled accurately assuming unending periodicity. Practical winding designs, in both Cartesian and cylindrical formats, balance the competing constraints imposed by the waveform shaping criteria. These winding structures are suitable for use with a variety of sensing elements for the magnetic field, including standard eddy current coils, Hall effect sensors, magnetoresistive elements, SQUIDs, and hybrid combinations of these elements.

In addition, when the goal is to discriminate between near-surface and deep material properties, multiple sensing elements can be placed across the footprint of the drive winding structures. In one embodiment, a linear array of sensing elements, at least one of which contains a GMR sensor and feedback coil, are placed adjacent to a linear segment of the drive winding. This facilitates the creation of property images as the array is scanned in a direction perpendicular to the array orientation. In another embodiment, a second linear array is placed parallel to the first array of sensing elements and offset by half a sensing element dimension in a direction parallel to the array orientation. This ensures that no areas are missed when the array is scanned over a material. The distance between the linear arrays and the linear drive segments, which affects the depth of sensitivity of the sensor response, can be adjusted to increase the sensitivity of a particular measurement. In another embodiment, a two-dimensional array of sensing elements, at least one of which contains a GMR sensor and a feedback coil, can be distributed throughout the footprint of the drive winding. In an embodiment where the drive winding has a cylindrical symmetry, the array of elements can go around the circumference of one of the drive windings. In addition, the shape of the sensing element coils or the feedback coil can be irregular and designed to match the spaces in the drive winding segments and the scan pattern. For arrays that use more than one GMR sensor, feedback coils can be wrapped around each individual GMR sensor or groups of GMR sensors can be encircled by a single feedback coil. Also, since the GMR sensor is sensitive to the orientation of the magnetic field, one or more of the GMR sensors can be oriented differently than the other sensors to provide sensitivity to other field orientations.

In another embodiment, a capability for edge detection and correction is possible with drive windings having linear drive segments by placing secondary elements both at the center of the primary and near the end-most winding segments. Since the field near the center of the primary is not significantly different for the infinitely periodic sensor versus the finite width sensor, the sensing elements near the center will be insensitive to the presence of the edge until the edge is substantially beneath the drive. In contrast, sensing elements placed near the edge respond to the fringing fields that are the first to be perturbed by the edge as the sensor is scanned off of the edge.

Another aspect of this invention is the realization that the relative motion between the magnetoquasistatic sensor and the material under test influences both the magnetic field distribution and the sensor response. The relative velocity changes the effective frequency of the excitation and alters the depth of penetration of the imposed magnetic field into the material under test.

In another embodiment, methods are described for determining the material properties from the measured values. In one method, two properties or parameter values associated with a measurement are determined from measured responses by performing a two-dimensional inverse interpolation. This interpolation is performed by searching through a database of responses, which can be visualized as grids, locating the grid cell that contains the target or measured point, identifying the parameter values associates with the edges of this grid cell, and performing a bilinear interpolation to determine the final values. In another method, the parameters are estimated using conventional least-squares minimization technique with the forward step of the calculation replaced by a table look-up procedure using a precomputed multi-dimensional database of responses. Since table look-up procedures are generally very fast compared to simulated response calculations, this permits real-time determination of the properties from the measurement values.

BRIEF DESCRIPTION OF THE DRAWINGS

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

DETAILED DESCRIPTION OF THE INVENTION

Figure 1:
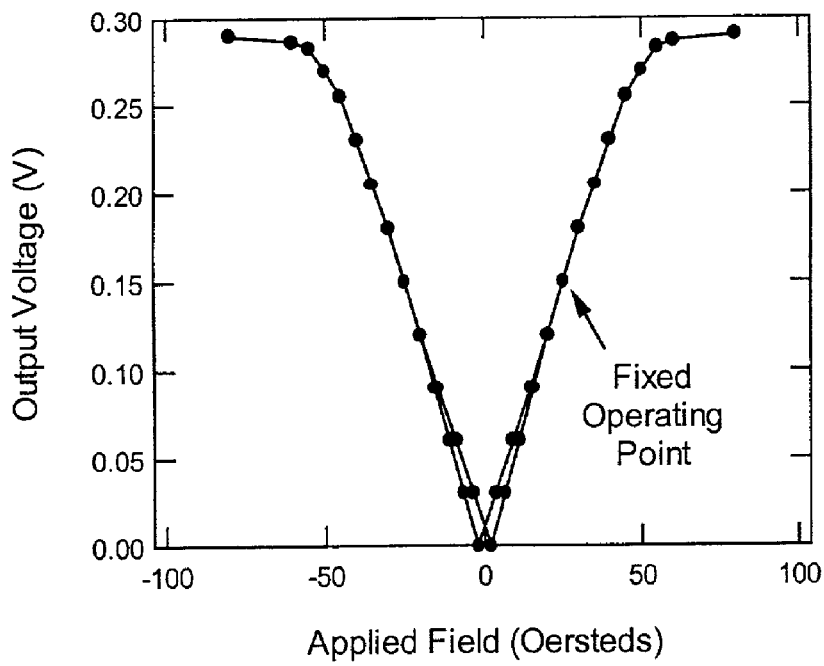
FIG. 1 is a typical transfer characteristic of a GMR magnetic sensor biased at 5 volts.

A description of preferred embodiments of the invention follows.

Traditional eddy current sensing devices have a limited capability for low frequency measurements where sensitivity to deep property variations are required. These limitations can be overcome by replacing the secondary winding with alternative secondary elements, such as a Hall effect sensors, magnetoresistive sensors, SQUIDS, and others, which respond directly to the magnetic flux density. As described in U.S. Pat. No. 5,793,206, the contents of which are incorporated herein by reference in its entirety, these alternative secondary elements can be incorporated into sensors having meandering drive windings. In one embodiment, a GMR magnetic field sensor is used. Although magnetic sensors based on the magnetoresistive effect are passive components with non-linear transfer characteristics and limited dynamic range, they do not have a lower bound on the operating frequency and are thus ideal for low frequency measurements. Indeed, dc or zero frequency measurements are possible with these giant magnetoresistive sensor elements. The shortcomings of the magnetic sensor are overcome by biasing into a linear operating regime and placing the sensor into a feedback loop configuration with a coil or secondary winding surrounding the magnetic sensor and driven to maintain a constant magnetic flux density at the sensor. This feedback loop increases the dynamic range of the sensor and the amplitude of the magnetic field that can be measured is only limited by the current driving capability of the associated feedback circuit. While the feedback loop reduces the operational frequency range for the GMR sensor, the GMR sensor with feedback loop allows operation over a wider frequency range than a single sensing coil. High frequency measurements with the hybrid structure can be performed by either running the magnetic sensor open-loop, with no feedback, or by measuring the response of the secondary winding directly, as with a traditional eddy current sensing device.

The inspection of ferromagnetic materials also motivates the development of sensors that can operate at low excitation frequencies. With these materials, local magnetic permeability variations are present as the residual stress varies throughout the material. This complicates measurements of the electrical conductivity of the material since the material conductivity and permeability cannot be independently measured at high frequencies. Lower the excitation frequency permits isolating the permeability variations from the conductivity variations.

Some progress has been made in adapting GMR sensors to non-destructive testing applications. Wincheski and Namkung have integrated a GMR with a self nulling probe driver coil to produce the Very Low Frequency (VLF) Self Nulling Probe. They have operated this device at excitation frequencies down to 135 Hz and have used it to detect an EDM notch at a depth of up to 10 mm (Wincheski, 2001). Others have attempted this as well by using conventional eddy current sensor designs (e.g., Rempt, 2001). These single element GMR sensors have demonstrated a capability to detect cracks under fastener heads and deep into lap joint structures. The inventions described here address both improved single sensing element designs and arrays with improved drive winding designs. In an embodiment of this invention, micro-fabricated arrays (or arrays of commercially available GMRs) are incorporated into drive winding designs to provide a high resolution, wide area imaging capability. Unique drive coil designs, both square wave and smoothly varying, that provide deep penetration while retaining geometric features that permit accurate modeling of field interactions, combined with high-resolution arrays of GMR sensors, permit imaging of sub-surface damage and geometric features.

Despite this progress, there are several complications associated with the use of GMR sensors in an eddy current probe. They have a highly nonlinear transfer characteristic. The nonlinearity is, in fact, very extreme, since the sensors are insensitive to the polarity of the magnetic field (see FIG. 1). For this reason, they are typically biased to an appropriate operating point by an independent magnetic field source, such as a permanent magnet or solenoid. Since the magnetic field effects a resistivity change, the sensors also need electrical biasing and an appropriate bridge configuration. Many of these issues can be addressed by placing the sensor in a feedback loop, as illustrated in FIG. 2.

FIG. 1 is a plot of the transfer characteristic of a commercially available magnetic sensor that has been used as a sensing element in an eddy current type sensor. The GMR sensor, manufactured by Nonvolatile Electronics, Inc., consists of four magnetic superlattice resistors, deposited on a common ceramic substrate, and connected in a bridge configuration. Two of the resistors are shielded from external magnetic fields while ferromagnetic flux concentrators are used to increase the effect of the magnetic field on the other two resistors. Several features of the giant magnetoresistive effect are evident in FIG. 1. First, the differential output voltage is independent of the polarity of the applied field, because either polarity leads to a departure from the fully antiparallel alignment. Second, at a certain field magnitude, about 50 Oe for this sensor, the output reaches a saturation value, corresponding to complete alignment of the ferromagnetic layers. And finally, the response shows some hysteresis.

The highly nonlinear nature of the transfer characteristic, especially near zero, makes it necessary to operate the sensor with a DC field bias, moving the operating point to the linear region of the characteristic. The biasing may be accomplished with a permanent magnet, but this has the undesirable side effect that, in addition to generating the constant bias field, it will perturb the field being measured. Alternatively, the sensor may be biased with an electromagnet. While DC biasing addresses the nonlinearity and hysteresis problems, a severe limitation still remains. Satisfactory operation is maintained only for fields with magnitudes that are small compared to the DC bias field. As the field magnitude increases, the response becomes more and more nonlinear, and for amplitudes on the order of the bias field, a polarity reversal occurs.

Figure 2:
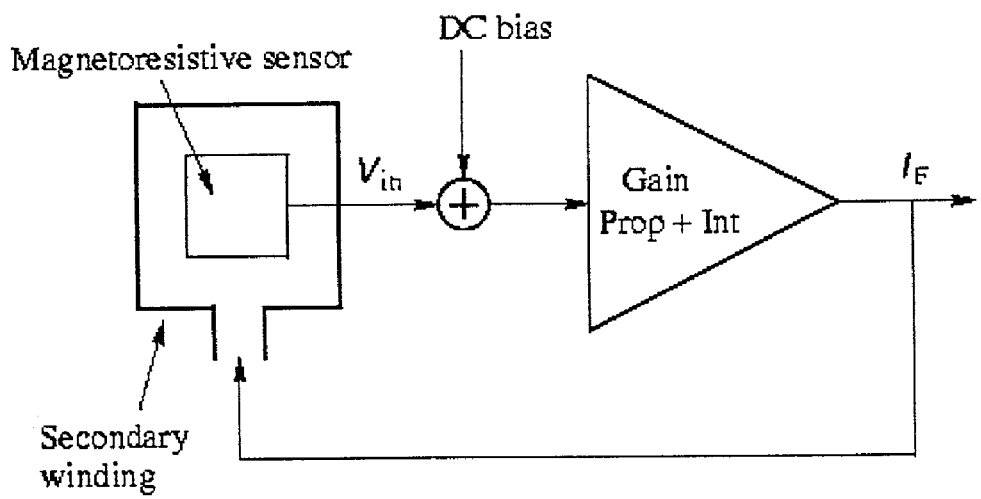
FIG. 2 shows the structure of the hybrid sensor feedback loop.

To address these limitations, the sensor can be placed in a feed back configuration with a secondary winding, as shown in FIG. 2 and described in Sheiretov (2001), the contents of which are incorporated herein by reference in its entirety. In this way the magnetic field at the GMR sensor remains nearly constant during operation, eliminating the effect of the nonlinear transfer characteristic, while maintaining sensitivity at low frequencies. The magnitude of the current in the secondary winding is taken as the output signal, and since the relationship between this current and the magnetic field for an air-core winding is linear, so is the transfer characteristic of the entire hybrid sensor structure. The magnetic field magnitude that this hybrid GMR sensor can measure is limited only by the magnitude of the field that the secondary winding can produce, which can be orders of magnitude higher than the saturation field of the GMR sensor. This dramatically increases the dynamic range of the GMR sensor and makes it's use far more practical than in alternative implementations with permanent magnets or electromagnets that provide a constant bias.

Another benefit of the feedback configuration is temperature stability. Since the measured quantities are currents in the windings, which are directly related to the magnetic fields, temperature dependence of the GMR sensor on winding resistance, etc. has no effect on the magnetometer response. This is critical since temperature variations have limited reproducibility and limit the use of many commercially available eddy current arrays. Goldfine and Melcher (U.S. Pat. No. 5,453,689, the contents of which are incorporated herein by reference in its entirey) solved the temperature sensitivity problem for inductive sensing elements by maintaining a gap between drive and sensing windings. Temperature stability is a key to the practical use of GMR sensors as well.

Another advantage of the feedback connection is for biasing the GMR sensor. Biasing the GMR sensor to the appropriate operating point is accomplished simply by adding an appropriate DC voltage offset at the input of the gain stage. This is much better than the alternative biasing methods described earlier, since correct biasing is maintained even if the position of the GMR sensor with respect to the bias source changes, which would not be true for biasing with a constant field source. This eliminates the need for complex alignment methods, since biasing at the correct level is automatic with the appropriate choice of circuit components. As a result, this feedback configuration provides the same sensitivity of a GMR sensor by itself while maintaining a linear transfer characteristic and a wider dynamic range.

There can be situations where this kind of feedback configuration may be inappropriate. The bandwidth of the hybrid sensor is limited by the dynamics of feedback loop, and is always narrower than open-loop operation. Therefore at high frequencies the sensor may need to be operated in an open-loop mode, although it is still possible to keep the loop closed at low frequencies in order to maintain the proper DC bias. This is not a severe limitation, since this magnetometer is not designed for high frequency operation, where it may be more appropriate to use a standard spatially periodic field eddy current sensor. An additional limitation of the feedback loop configuration is that in an array arrangement, the feedback windings of adjacent elements will be coupled to each other, potentially leading to inter-channel cross talk. It is generally possible to compensate for this in the models for the sensor responses, but it is better to avoid such situations by appropriate shielding or by open-loop operation.

Figure 3:
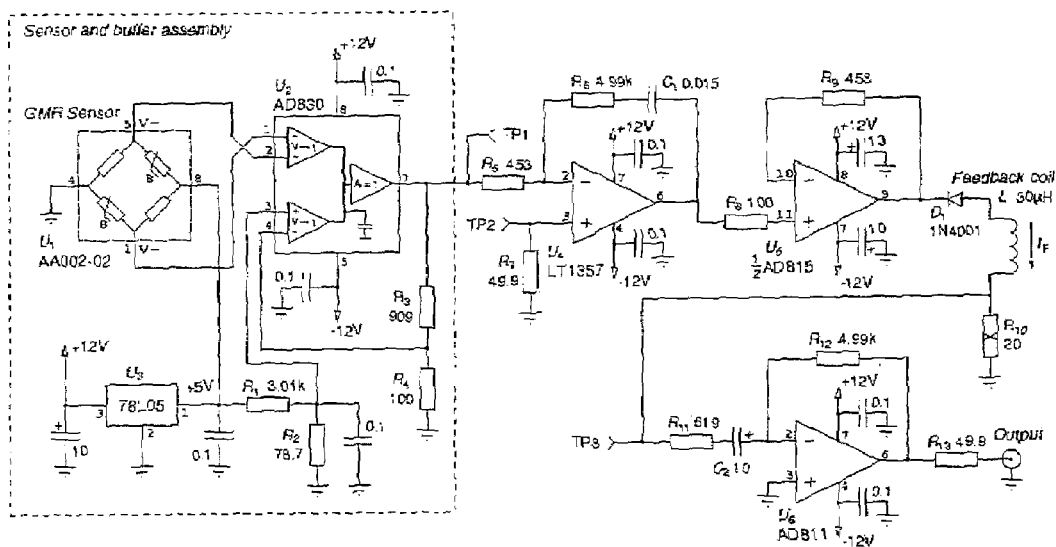
FIG. 3 shows a schematic for a feedback and interface circuit.

A full schematic of the electronic circuit used to implement the feedback loop, biasing, and interface, is shown in FIG. 3. The resistor bridge of the GMR sensor is shown as $U_1$. The output impedance of the sensor is relatively high, on the order of 40 k$\Omega$, and in order to avoid parasitic signal and noise pick-up, as well as extra phase shift due to cable capacitance, a buffer amplifier is placed in close proximity to the sensor. The entire buffer stage assembly XX also implements the sensor DC biasing scheme. The buffering is accomplished with a high bandwidth instrumentation amplifier $U_2$. The voltage regulator $U_3$ is needed to ensure constant sensor voltage and field biasing. The DC operating point is set by the voltage divider implemented with $R_1$ and $R_2$. This first stage also has gain of 10. The loop gain and compensation, described later, are implemented in the $U_4$ amplifier stage. The secondary winding is driven by the high power video amplifier $U_5$, connected as a unity gain follower. Since $U_5$ is a current feedback operational amplifier, it is necessary to include resistor $R_9$, which is also used to set the bandwidth of the stage. The current $I_F$ through the secondary feedback winding is measured as the voltage across a precision zero-inductance power resistor $R_{10}$ connected in series. The last stage, implemented with $U_6$, is used as a coaxial cable driver. It also eliminates the DC component of the signal and brings the output magnitude to the optimal input levels of the impedance analyzer instrumentation. For constant field measurements, which do not require an impedance analyzer, the output signal is taken at test point 3.

Because of the rectifying effect of the GMR sensor, the overall polarity of the feedback loop depends on the direction of the magnetic field. This means that as the circuit is initially powered up, it may enter a positive feedback mode, which is unstable, leads to the output of $U_5$ saturating at the positive supply voltage level, and renders the system inoperable. On the other hand, if the correct operating point is established first, then the feedback will be negative and the loop will then remain stable, unless the magnetic field reaches such magnitude that the driver of the secondary winding cannot keep up. In that case the loop may again become unstable. This complication is a direct consequence of the GMR sensor transfer characteristic and cannot be avoided. It is therefore necessary to implement some external mechanism which would detect the faulty condition and reset the loop by forcing the output to be near the operating point. A much simpler remedy, used in this implementation, is to ensure that the current through the secondary winding is always negative, by connecting a diode $D_1$ in series with it. This resolves the stability problem and ensures that the feedback loop always recovers to the proper operating point. However, it also introduces a limitation. While the magnitude of the measured field is unlimited in the positive direction, in the negative direction it may not exceed the bias field. Although this compromise is acceptable for the prototype magnetometer, in a more general setting it may be necessary to incorporate an auxiliary "watch dog" circuit of the kind described above.

Another consideration for the feedback circuit is the stability of the circuit and the bandwidth for the loop. Ignoring for the moment the $U_4$ stage, the ideal open-loop transfer characteristic consists of a single pole at $\omega=R_{10}/L$, introduced by the relationship between driver output voltage and secondary winding current $I_F$. In the ideal case where this is the only pole, the loop is always stable and its bandwidth can be increased indefinitely by increasing the loop gain. In practice all operational amplifiers have a limited bandwidth and parasitic capacitances always introduce extra phase. One approach to find the optimal loop gain is to measure the open loop transfer function experimentally. This is done by shorting out $R_6$ and $C_1$, transforming $U_4$ into a voltage follower, applying a signal at test point 2, and measuring the relative magnitude and phase of the voltage at test point 1. The input signal must include an appropriate DC offset, needed for proper biasing of the GMR sensor. As expected, the phase angle reaches $-45°$ at about 100 kHz, the frequency of the pole. The phase angle reaches $-90°$ at about 350 kHz, which is chosen as the loop bandwidth, allowing for plenty of phase margin, 90°. The gain of the $U_4$ amplifier stage is chosen to be equal to the inverse of the open-loop magnitude at this frequency. The presence of $C_1$ in series with $R_6$ is useful, though not required, because it introduces a pole at $\omega=0$ and a zero at $\omega=1/(R_6 C_1)$ near 2 kHz. As a consequence the feedback loop error, given by the voltage at test point 1, is zero at DC and small at low frequencies.

When modeling the response of the sensor in this feedback loop, the field generated by the current in the feedback winding must be considered. One cannot assume that the output signal $I_f$ is directly proportional to the imposed field at the origin since the secondary winding is a solenoid tightly would around the GMR sensor. Experiments showed that this assumption is not justified since the field created by the secondary winding is influenced by the proximity and properties of the material under test. As a result, the net field imposed on the GMR sensor at the origin, created by the drive winding and the current through the secondary winding, must be considered when calculating the transfer function (ratio of the secondary current to the drive current) for the feedback sensor structure. Normalizing the response of the sensor to a measurement in air, as with a standard air-calibration measurement procedure, then allows the absolute properties of the material under test to be determined.

In addition to the frequency, the geometry of the drive winding also affects the depth of penetration of the magnetic field into the test material. Passing a current through the drive winding creates a magnetic field that has spatial modes determined predominantly by the geometry of the drive winding. In general, the shorter of the skin depth into the material or the wavelength of the dominant spatial mode limits the depth of penetration. Spatially periodic field eddy-current sensors, designed to create a single dominant spatial mode, have been used to measure foil thickness, characterize coatings, and measure porosity, as well as to measure property profiles as a function of depth into a part, as disclosed in U.S. Pat. No. 5,015,951, the contents of which are incorporated herein by reference in its entirety, and U.S. Pat. No. 5,453,689. Novel nonperiodic shaped-field drive winding structures, also designed to create a single dominant spatial mode, have also been disclosed, for example, in U.S. patent application Ser. No. 09/488,241, the contents of which are incorporated herein by reference in its entirey. For controlling the magnetic field shape, discrete distributed drive windings are used. Rather than driving each current segment independently, one or more continuous winding conductors are used, with the correct current profile obtained by changing the number of winding turns within each segment.

Figure 4:
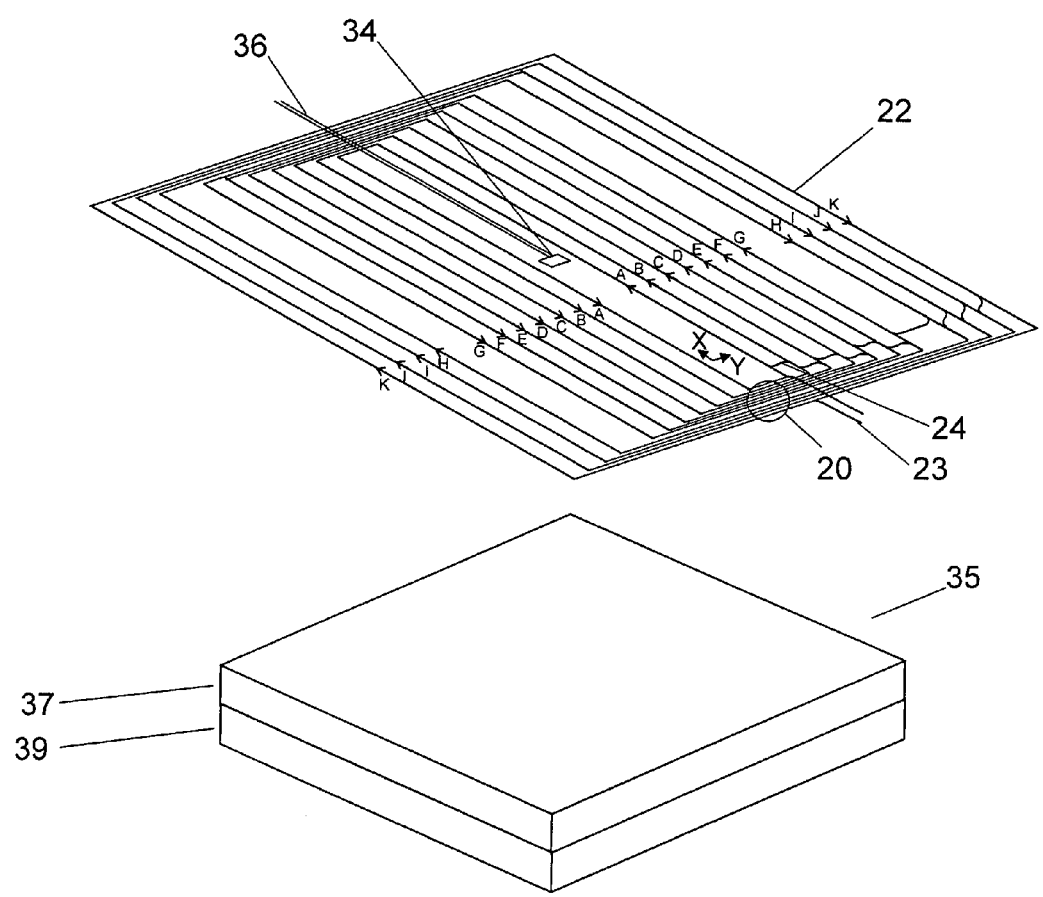
FIG. 4 shows the structure of a shaped field drive winding in cartesian coordinates.
Figure 5:
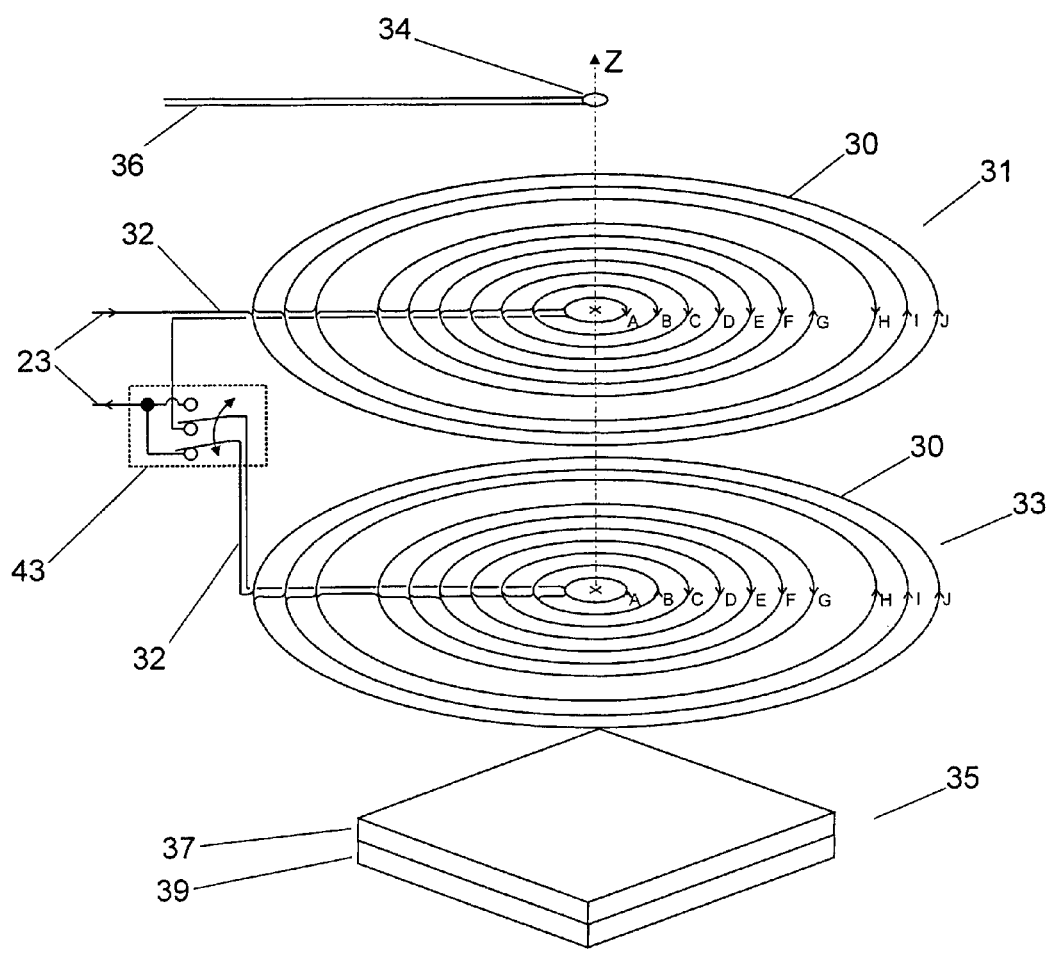
FIG. 5 shows the structure of a rotationally symmetric shaped field drive winding.
Figure 8:
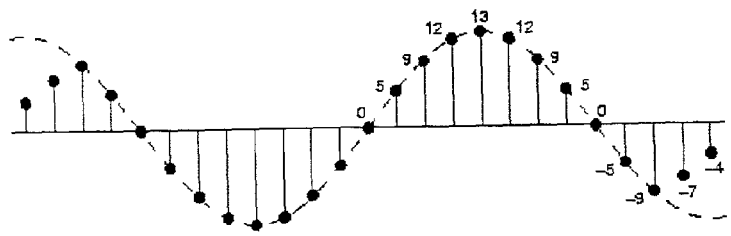
FIG. 8 Number of winding turns for the rectangular sensor with no net dipole moment, according to Table 1, the sinusoidal envelope function being shown with a dashed line, and the number of turns not falling exactly on the curve, since they need to be integers.
Figure 9:
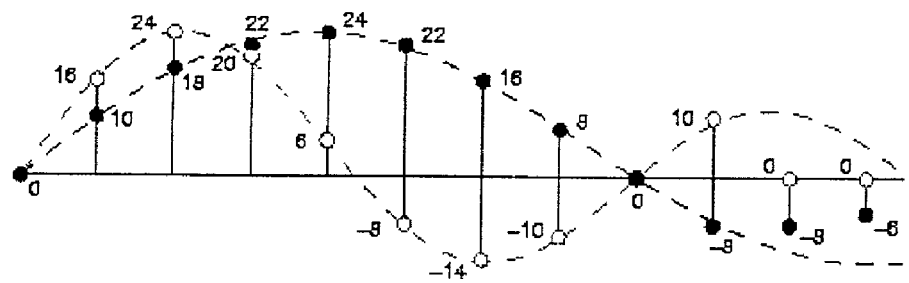
FIG. 9 shows a winding pattern for the circular magnetometer that enables two different fundamental wavelengths, determined by the polarity of the connection, with the filled circles corresponding to long wavelength operation, and the hollow circles corresponding to short wavelength operation.

Shaped field winding patterns for the drive winding can be created in a variety of geometries. As an example, FIG. 4 shows windings comprised of rectangular loops for a Cartesian coordinate pattern. Terminal connections to these loops are made through the wires 23 and interconnections between the loops are made through the wires 24. The number of turns in each segment 22, denoted by the capital letters A through K, is varied so that the shape of the cross-sectional current distribution in the y direction can be adjusted as necessary. Continuity of the current is maintained with the side connections 20. These side connections are typically placed far enough apart so that no variations in the x direction need to be considered when modeling the sensor response. An example winding current distribution designed to excite a singular Fourier mode for the magnetic field is illustrated in FIG. 8 and listed in Table 1. For each segment, the sign for each value indicates the current direction while the integer indicates the number of conducting segments or relative current magnitude. Another example is the rotationally symmetric cylindrical geometry FIG. 5, where the number of turns and current direction in each discrete circular loop 30 is varied to shape the field. Interconnections between each segment are made with tightly wound conductor pairs 32 to minimize fringing field effects. A GMR sensor 34, with feedback controlled coil, is placed at the center of the concentric circular drive windings. Sensor 34 may also be a coil, a SQUID sensor, or a Hall effect sensor. Connections to this sensing element are made with a tightly wound conductor pair 36. Both the number of turns and the polarity of the windings (current direction) can be varied in the drive winding segments. In this case, there are two sets of drive windings (31 and 33), with each loop in the radial direction aligned with one another and placed nearby so that the distance in the z direction between the windings and also the sense element 34 are small compared to the largest loop diameter, which allows more than one fundamental spatial mode. As described later, the polarity of the connection 32 determines which of the two current drive patterns (with different fundamental spatial wavelengths) is excited. This provides two distinct field depth of penetration conditions and permits improved multiple property measurements for layered media. The capital letters for each winding indicate the number of turns and the arrows on each indicate that the winding direction can also be changed between loops. The test material 35 can be a substrate 39 having a magnetizable foam layer 37 of known thickness. An example winding distribution designed to excite a singular Fourier-Bessel mode for the magnetic field is illustrated in FIG. 9. This example uses the winding turn and current distribution listed in Table 3, where the patterns A and B correspond to the turn distributions of the windings 31 and 33.

Once the sensor response is obtained, an efficient method for converting the response of the GMR sensor into material or geometric properties is to use grid measurement methods. These methods map the magnitude and phase of the sensor response into the properties to be determined. The sensors are modeled, and the models are used to generate databases correlating sensor response to material properties. Only by constructing these measurement grids off-line is it possible to convert to material properties in real-time. The measurement grids are two-dimensional databases that can be visualized as "grids" that relate two measured parameters to two unknowns, such as the conductivity and lift-off (where lift-off is defined as the proximity of the test material to the plane of the sensor windings). For coating characterization or for inhomogeneous layered constructs, three-dimensional grids (or higher order grids), called lattices (or hyper-cubes), are used. Similarly, a model for the GMR sensor with feedback loop and circular drive windings was developed and used to generate measurement grids, which were then used to interpret sensor response. Alternatively, the surface layer parameters can be determined from numerical algorithms that minimize the least-squares error between the measurements and the predicted responses from the sensor.

It is also possible to combine the grid measurement methods with a least-squares minimization method for a hybrid inverse estimation method. In this case, the standard error function minimization technique of standard minimization methods would be used. The forward steps of the estimation that require calculations of the response from the model would be replaced by forward grid lookup routines evaluated on precomputed databases of responses. Standard grids could be used for two-unknowns, lattices for three unknowns, and higher dimensional databases for greater unknowns. This has the advantage of being much faster than the standard minimization algorithm, provides a multiple unknown estimation capability, may incorporate data from many measurements taken under a variety of conditions, and works in cases when post-processing of simulated results is necessary, such as to account for parasitic or otherwise unmodeled effects. The disadvantages are that the databases need to be generated before hand and the method is not guaranteed to find a solution. This latter disadvantage is also a limitation of standard minimization techniques.

An advantage of the measurement grid method is that it allows for real-time measurements of the absolute electrical properties of the material. The database of the sensor responses can be generated prior to the data acquisition on the part itself, so that only table lookup operation, which is relatively fast, needs to be performed. Furthermore, grids can be generated for the individual elements in an array so that each individual element can be lift-off compensated (or compensated for variation of another unknown, such as permeability or coating thickness) to provide absolute property measurements, such as the electrical conductivity. This again reduces the need for extensive calibration standards. In contrast, conventional eddy-current methods that use empirical correlation tables that relate the amplitude and phase of a lift-off compensated signal to parameters or properties of interest, such as crack size or hardness, require extensive calibrations and instrument preparation.

One of the other considerations for the drive winding structures is the decay of unintended or stray fields away from the sensor. These stray fields, and their decay pattern, can be understood qualitatively by considering the far-field decay patterns from multipole sources. For example, the drive winding may have a net dipole moment such that, at distances much larger than the sensor wavelength, the magnetic field approaches the form of a field generated by a magnetic dipole at the origin. The net dipole moment of concentric-drive windings will not be zero if each winding forms a current loop of non zero area, and the effective magnetic moments of all these loops point in the same direction.

Near the sensor surface the magnetic field decays essentially exponentially, at a rate determined by its spatial wavelength and the skin depth in the medium. Far from the sensor the fields fall off at a rate determined by the lowest order multipole moment excited by the sensor. Ideally, this will be a high order moment, since it is desirable for the sensor to lose sensitivity quickly with distance. Otherwise the sensor response will be affected by the presence of magnetizable and/or conducting objects in its vicinity, even if they are much farther than the material under test. For example, internal structural supports may interfere with mapping of corrosion in an aircraft lapjoint. Whereas this effect may be small, even compared to other unmodeled effects, it can change with time, as objects near the sensor are moved, or when the sensor is moved to inspect a new location. Thus, it cannot be eliminated via calibration and will result in a lack of reproducibility.

Figure 6:
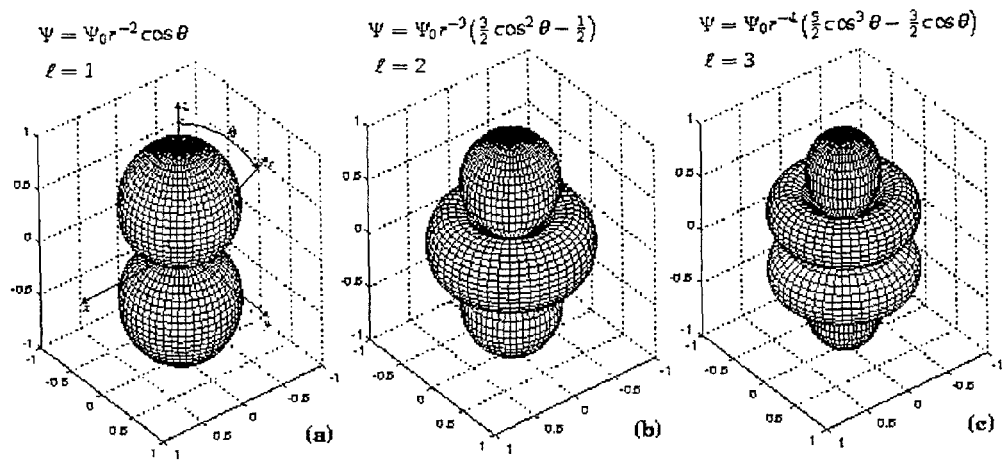
FIG. 6 Equipotential surfaces, $\psi(r, \theta, \phi)=\psi_0$, of the scalar magnetic potential for multipole moments with no $\phi$ dependence.
Figure 7:
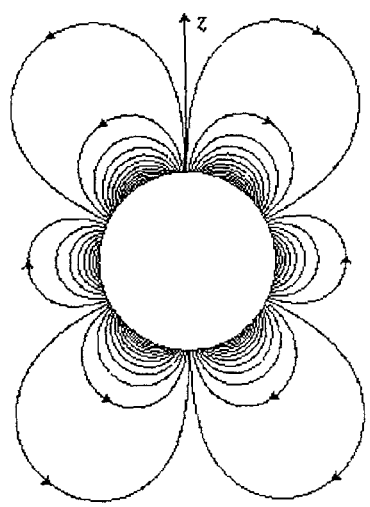
FIG. 7 Magnetic field lines for l=3 "octopole" moment potential.

For magnetic fields, the lowest order multipole solution possible to Laplace's equation in spherical coordinates is the dipole, whose scalar magnetic potential decays as $r^{-2}$. FIG. 6 shows the equipotential surfaces of the scalar magnetic potential for the three lowest order rotationally symmetric multipole modes. The "quadrupole" (l=2) mode cannot be excited by these magnetic sensors, since it is even with respect to z, whereas flipping the sensor upside down reverses the current direction in all windings, changing the sense of all magnetic fields. If the dipole moment is eliminated, the next dominant mode is the "octupole," whose magnetic field lines are shown in FIG. 7. The potential of this mode has an $r^{-4}$ dependence, which means that the magnetic field intensity falls off as $r^{-5}$. In practice the decay rate of the octupole is fast enough so that canceling out the dipole moment is sufficient to eliminate unwanted long range sensitivity.

For the net dipole moment of the drive winding to cancel, the contributions of each individual winding segment (including selected numbers of turns to shape the field) must sum to zero. To satisfy this constraint, the sensor must include a fraction of a wavelength past the end of the single period. For this additional fraction of a wavelength, the current is in the opposite direction. Since the number of winding turns is always an integer, it is impossible to satisfy the zero-sum constraint exactly while at the same time strictly following the sinusoidal envelope function. Another consideration in choosing the numbers tapering off the current towards the ends of the sensor in order to avoid rapid changes in the primary current distribution, which would result in more energy in higher order Fourier modes, and consequently, a reduction of the sensitivity at greater depths. A compromise between these considerations for a shaped field sensor in Cartesian coordinates (drive segments placed at different locations in the y-direction and assuming the segments are long enough in the x-direction so that no variation in the field distribution in the x-direction needs to be considered) is shown in Table 1, which lists a winding pattern that results in no net dipole moment. The winding turns are also plotted in FIG. 8. The current in the last two segments deviates from the sinusoid but prevents the generation of the higher order spatial modes.

TABLE 1

Drive winding pattern for a rectangular magnetometer having no net dipole moment.

| j = y/h | 0 | 1 | 2 | 3 | 4 | 5 | 6 | 7 | 8 | 9 | 10 | 11 | 12 |
|---|---|---|---|---|---|---|---|---|---|---|---|---|---|
| Winding turns $\omega_1$ | 0 | 5 | 9 | 12 | 13 | 12 | 9 | 5 | 0 | -5 | -9 | -7 | -4 |

It is also possible to change the fundamental wavelength of the current excitation without changing the geometry of the sensor, by changing the current distribution in the primary winding segments. Since the depth of sensitivity of the sensor depends on the imposed spatial wavelength, the use of more than one excitation wavelength will provide some information on how material properties change with depth. Furthermore, the use of more than one wavelength within the same footprint has the advantage that the lift-off (distance between sensor and material) will be the same for both modes of operation. This is very useful when there are more than two unknown parameters and measurements under two different applied magnetic field distributions are necessary to determine all unknowns uniquely. This may be accomplished by supplying an independent current drive for each segment and changing the relative magnitudes of these drives to follow an appropriate envelope function with the needed wavelength. A more practical approach avoids the need for multiple drives by using two or more independent winding circuits and switching the relative current direction between them.

As an example, consider the winding distribution of Table 2 for a rectangular or Cartesian sensor. Two windings, A and B, and the number of turns each has in every current segment, are shown in this table. As before, negative turns indicate that they are wound in the opposite direction. When the two windings are driven in the same polarity, the resulting current distribution excites a mode with a fundamental wavelength equal to the length of the sensor. If, on the other hand, the two windings are driven with opposite polarities, the resulting excitation has a fundamental wavelength equal to one-half of the sensor length. This approach can be followed in both Cartesian coordinates and cylindrical coordinates. Table 3 shows the winding pattern for a magnetometer having circular symmetry with the current distribution designed to match a first order Bessel function. This distribution is illustrated in FIG. 9, where the filled circles correspond to the A+B connection and the hollow circles correspond to the A−B connection. The curves show the envelope functions. The number of turns do not fall exactly on the curves because they need to be integers. The number of turns in the last two windings are tapered off in order to avoid rapid changes in the primary current distribution. Envelope distributions following a Bessel function were used since these functions arise when modeling the circularly symmetric versions of the magnetometer. Note that rotationally symmetric magnetoquasistatic and electroquasistatic sensor geometries are suitable for measurements on circularly symmetric components or when a dependence on sensor directionality is undesired.

placed near the edge respond to the fringing fields that are the first to be perturbed by the edge as the sensor is scanned off of the edge.

Practical winding designs, in both cartesian and cylindrical formats, balance the competing constraints imposed by the waveform shaping criteria. These winding structures are suitable for use with a variety of sensing elements for the magnetic field, including standard eddy current coils, Hall effect sensors, magnetoresistive elements, SQUIDs, and hybrid combinations of these elements.

TABLE 2

Two-wavelength winding pattern for a rectangular magnetometer.

Nominal Turns per Segment

| A     | 0 | 14 | 22 | 21 | 13 | 3   | -4  | -4  | 0 | 4   | 4   | -3  | -13 | -21 | -22 | -14 | 0 |
|-------|---|----|----|----|----|-----|-----|-----|---|-----|-----|-----|-----|-----|-----|-----|---|
| B     | 0 | -4 | -4 | 3  | 13 | 21  | 22  | 14  | 0 | -14 | -22 | -21 | -13 | -3  | 4   | 4   | 0 |
| A + B | 0 | 10 | 18 | 24 | 26 | 24  | 18  | 10  | 0 | -10 | -22 | -24 | -26 | -24 | -18 | -10 | 0 |
| A - B | 0 | 18 | 26 | 18 | 0  | -18 | -26 | -18 | 0 | 18  | 26  | 18  | 0   | -18 | -26 | -18 | 0 |

TABLE 3

Two-wavelength winding pattern for a circularly symmetric magnetometer.

Nominal Turns per Segment

| A     | 13 | 21 | 21 | 15 | 7  | 1   | -1  | 0   | 1  | -4 | -3 |
|-------|----|----|----|----|----|-----|-----|-----|----|----|----|
| B     | -3 | -3 | 1  | 9  | 15 | 15  | 9   | 0   | -9 | -4 | -3 |
| A + B | 10 | 18 | 22 | 24 | 22 | 16  | 8   | 0   | -8 | -8 | -6 |
| A - B | 16 | 24 | 20 | 6  | -8 | -14 | -10 | 0   | 10 | 0  | 0  |

The shaping of the imposed magnetic field allows the sensors to be designed with a deep depth of sensitivity to the test material properties and a minimal sensitivity to unmodeled effects distant from the test material.

Near the sensor surface the magnetic field, in the quasistatic limit, decays essentially exponentially, at a rate determined by its spatial wavelength and the skin depth in the medium. For a deep depth of sensitivity into the test material, it is generally desirable to maximize the energy in the dominant spatial mode for the sensor, which has the fundamental spatial wavelength. Drive winding designs that gradually taper the current densities to zero near the ends of the winding structure tend to have less energy in the higher order spatial modes than designs that have abrupt changes or discontinuities in the current density at the ends. To reduce sensitivity to the higher order spatial modes, which have shallower penetration depths, drive-winding designs that gradually reduce the current density to zero near the ends of the winding structure should be used. Alternatively, if simultaneous measurements of both deep and shallow penetration depths are desired, then drive-winding designs that have abrupt changes or discontinuities in the current density at the ends could be used. In addition, when the goal is to discriminate between near-surface and deep material properties, multiple sensing elements can be placed across the footprint of the array. The trade-off is in the data acquisition across parallel channels, lead connections, and switching of excitations as described in the next paragraph. In addition, for the Cartesian geometry, a capability for edge detection and correction by placing secondary elements both at the center of the primary and near the end-most winding segments is possible. Since the field calculation models show that the field near the center of the primary is not significantly different for the infinitely periodic versus the finite width sensor, the sensing elements near the center will be insensitive to the presence of the edge until the edge is substantially beneath the drive. In contrast, secondaries Several sets of measurements have been performed with a circularly symmetric shaped field magnetometer. These measurements used the GMR eddy current sensor with drive illustrated in FIG. 9. A simple one-point air calibration method is used for all of these measurements. This means that the sensor response when over the test material was normalized by the sensor response in air, away from any conducting or magnetic materials. The measurement results are then processed with measurement grids to provide absolute property measurements, such as electrical conductivity, magnetic permeability, material thickness, and sensor proximity (lift-off). The absolute property measurement capability eliminates the need for extensive, and in some cases any, calibration sets. Even if reference calibrations are performed, possibly to improve the accuracy of the property estimation, only a single calibration material may be required. Air and reference part calibration methods have previously been described for square wave meandering winding constructs in U.S. Pat. No. 6,188,218, the contents of which are incorporated herein by reference in its entirety. The discrete segment Cartesian and circular geometry sensors described herein can also be calibrated in this fashion because the sensor response can be accurately modeled. In principle, air calibrations in this context can be performed with any sensor whose response can be accurately modeled.

Figure 10:
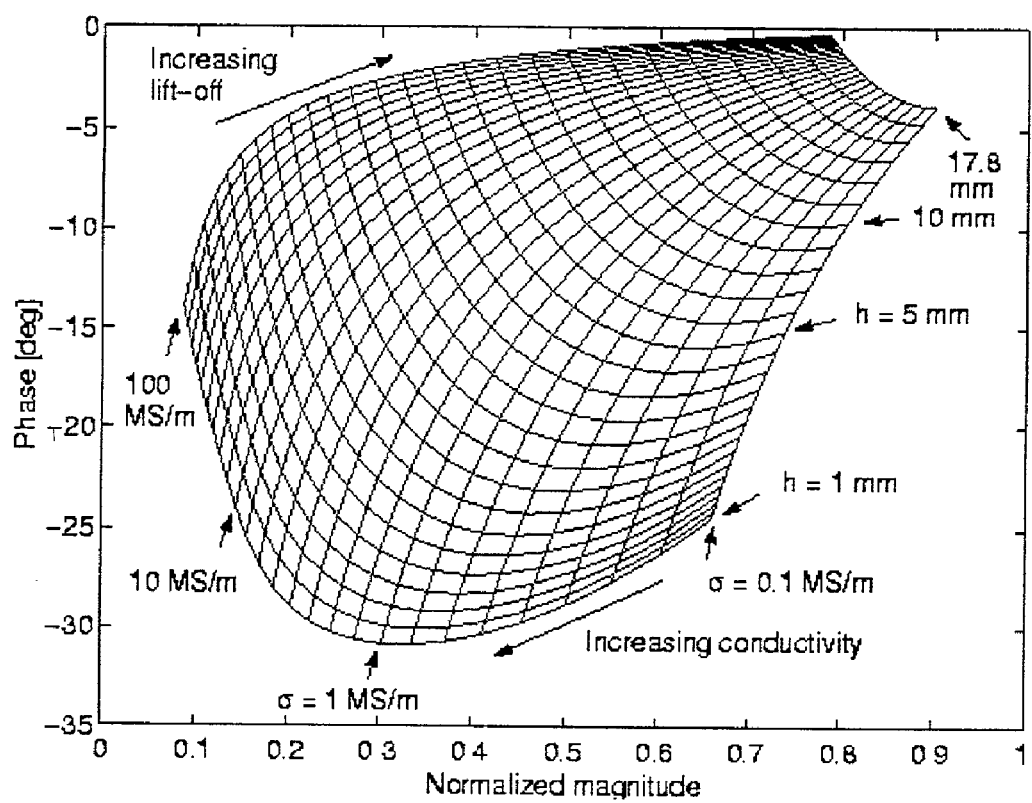
FIG. 10 shows conductivity/lift-off measurement grid for circular sensor at 12.6 kHz.

FIG. 10 shows the measurement grid for conductivity/lift-off measurements with three different materials, in the form of metal plates, over a range of lift-off values. Since both the conductivity and the lift-off parameters vary over a relatively large range, the parameter values for this grid are chosen on a logarithmic scale. The grid cell area is a measure of the sensitivity of the measurement in that region of the grid. The measurements are carried out at 12.6 kHz. Placing plastic shims between the sensor and the metal plates varied the lift-off.

Figure 11:
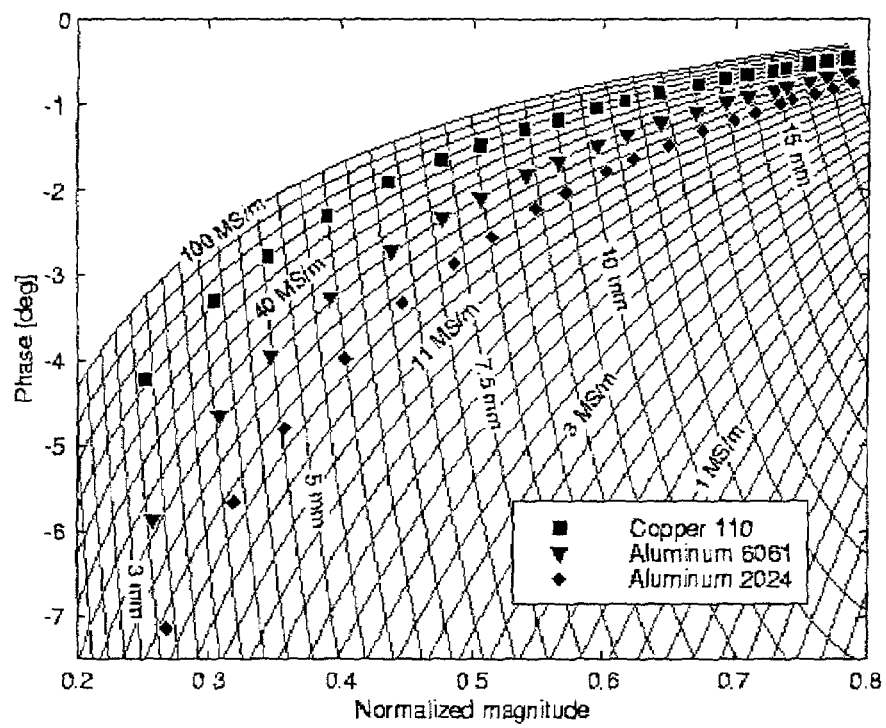
FIG. 11 shows results of conductivity/lift-off measurements with the circular magnetometer.

The results are shown in FIG. 11. The three data sets follow lines of constant conductivity very closely. As listed in Table 4, the measured lift-off values were in excellent agreement with the nominal values. Only the first 12 sets are listed, due to the lack of sensitivity at higher lift-off values, as illustrated by the narrowing of the grid cells in FIG. 11.

Figure 12:
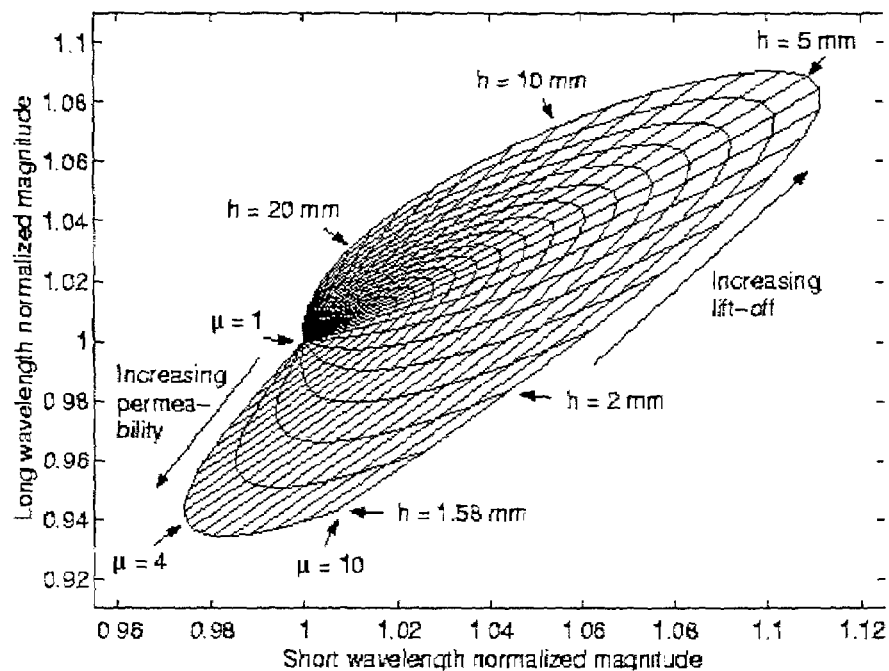
FIG. 12 shows a two wavelength magnitude/magnitude permeability/lift-off grid for a circular sensor with DC excitation.

The lowest value of the lift-off, 3.3 mm, corresponds to measurements with no shim, and is equal to the effective depth of the windings below the surface of the sensor. This amount has been added to the data in the last column, after having been estimated by taking the average of the difference between the magnetometer estimated values and the measured shim thicknesses. This number is quite reasonable, given that the average depth of the grooves is on the order of 3 mm, and that the winding thickness, about 2 mm, is not considered by the model. The conductivity data in Table 4 are also in good agreement with values reported in the literature. There appears to be an optimal range of the lift-off, 5–7 mm, where the estimated conductivity is most accurate. This is reasonable since sensitivity is lost at higher lift-offs, while a close proximity to the sensor windings is also not desirable since the effects of the non-zero winding thickness then become more significant. These conductivity results are also remarkable good considering that this measurement was carried out with no calibration standards and with a single air calibration point, the model for the sensor response is relatively simple, and no empirical data have been used to determine the sensor response. If it is necessary to perform a very exact conductivity measurement, then a two-point reference part calibration is recommended, with the properties of the two reference parts (or the same part at two lift-off values) bracketing the properties of the unknown part.

become real numbers (as opposed to the complex numbers that are used when the frequency is non-zero) and one measurement provides only one degree of freedom for determining the properties of the material under test. A magnitude/magnitude measurement grid used for parameter estimation is shown in FIG. 12. The spiral nature of the grid is due to the influence of the material under test on the feedback loop transfer function. This behavior is explained as follows: In general, as a magnetizable material is brought closer to the sensor windings, the magnitude of the signal increases, because the material tends to concentrate the magnetic flux. However, as the lift-off is reduced even further, this field concentration effect begins to affect the secondary feedback winding too, and since its radius is much smaller than the radii of the segments of the primary winding, this effect begins to dominate the overall magnetometer transfer function, reducing the magnitude.

This type of measurement is completely analogous to the dielectrometer measurements where the permittivity of a material is to be determined, as opposed to the permeability of a material. Both types of measurements use the signal magnitudes at two different spatial wavelengths to estimate the permittivity or permeability of a sample with known thickness, and its distance from the sensor electrodes or

TABLE 4

Measurement results corresponding to FIG. 11.

| Data Set | Conductivity [MS/m] | | | Lift-off [mm] | | | Nominal Lift-off [mm] |
|---|---|---|---|---|---|---|---|
| | Cu 110 | Al 6061 | Al 2024 | Cu 110 | Al 6061 | Al 2024 | |
| 1 | 59.2 | 29.5 | 18.0 | 3.2 | 3.3 | 3.3 | 3.3 |
| 2 | 59.2 | 28.9 | 17.8 | 4.0 | 4.1 | 4.1 | 4.1 |
| 3 | 58.7 | 28.7 | 17.8 | 4.7 | 4.8 | 4.5 | 4.8 |
| 4 | 58.3 | 28.6 | 17.6 | 5.5 | 5.6 | 5.6 | 5.6 |
| 5 | 57.8 | 28.3 | 17.6 | 6.4 | 6.5 | 6.5 | 6.5 |
| 6 | 57.1 | 28.1 | 17.5 | 7.3 | 7.1 | 7.3 | 7.3 |
| 7 | 55.7 | 27.4 | 17.3 | 7.9 | 8.0 | 8.0 | 8.0 |
| 8 | 56.1 | 27.5 | 17.4 | 8.7 | 8.9 | 8.8 | 8.8 |
| 9 | 54.3 | 26.8 | 17.1 | 9.4 | 9.5 | 9.4 | 9.4 |
| 10 | 55.2 | 27.0 | 17.2 | 10.2 | 10.3 | 10.3 | 10.2 |
| 11 | 53.5 | 26.4 | 17.0 | 10.8 | 10.9 | 10.9 | 10.9 |
| 12 | 53.0 | 26.3 | 16.7 | 11.7 | 11.7 | 11.7 | 11.7 |

These results confirm the validity of the model for this cylindrical coordinate sensor. Additional measurements were made to illustrate the unique advantages of the GMR magnetometer by using frequencies and material thicknesses outside the range of standard eddy current sensors.

One example measurement illustrating the unique capabilities of the cylindrical GMR based magnetomer is the use of two-different spatial wavelengths and a DC excitation to determine the permeability of a layer of known thickness and it's lift-off from the sensor surface. This type of measurement could apply, for example, to the measurement of the proximity and permeability of a low observability (LO) coating, such as a magnetizable foam layer. This type of measurement is unique in three important ways: (1) quasi-static sensors are generally not operated in the fully static regime at DC, (2) two-wavelength magnetometry has never been demonstrated, and (3) the wavelength of the sensor can be changed dynamically, with the material under test still in place. These are all useful capabilities, especially in measuring magnetizable materials without the limitation caused by the skin depth effect.

With DC operation the diffusion term in the differential equations disappears and the problem becomes completely parallel to dielectrometry measurements on insulating materials. All amplitudes in the models for the sensor response windings. The magnetizable layer consists of 1 mm thick polymer, containing ferromagnetic particles suspended in the polymer foam.

Figure 13:
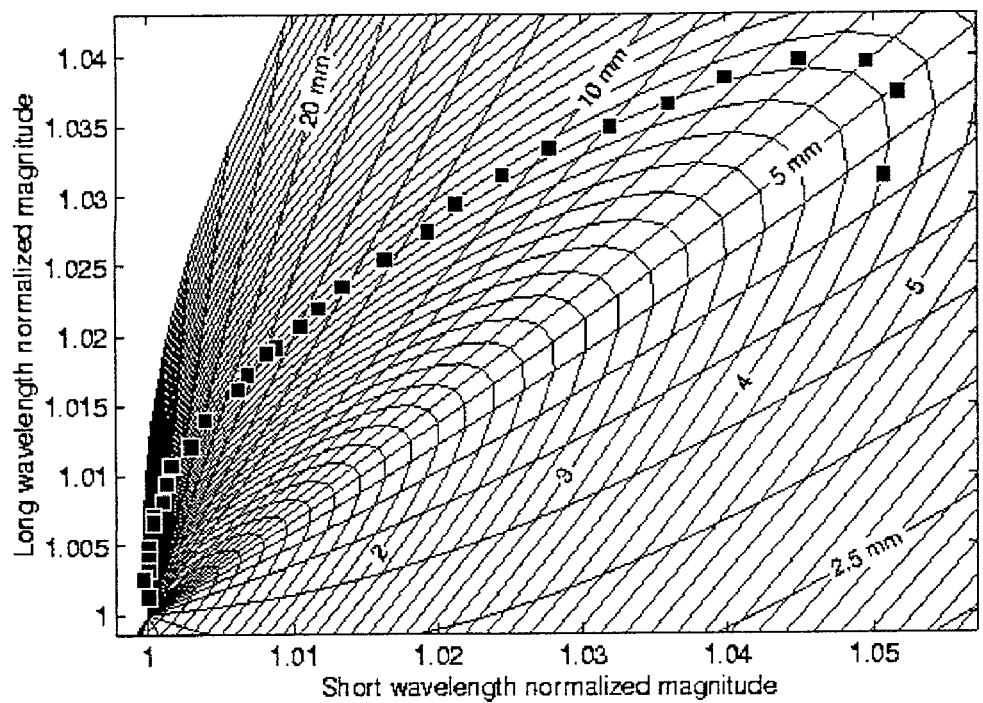
FIG. 13 shows the results of permeability lift-off measurements with the circular GMR magnetometer and a 1 mm thick magnetizable foam layer.

Representative measurement results, with the lift-off varied by placing plastic shims between the material under test and the sensor, are shown in FIG. 13, and listed in Table 5. Performing the measurements at DC required some special procedures. On the one hand, the only necessary equipment is a power supply and a voltmeter so that the measurement is relatively simple. On the other hand, the accuracy of the measurement is lower than that possible with AC excitation. When operating the sensor at a specific frequency, the magnitude of this frequency component in the output signal can be measured very accurately by mixing it with a signal at the same frequency from the same source and passing the resulting signal through a low pass filter. The resulting DC component is then related to the magnitude of the output signal. The signal can be integrated over many cycles, which results in a very accurate measurement of the transfer function at this frequency. With DC operation this frequency mixing technique is not available. Furthermore, it is not practical to average the signal over a long time, because outside factors affecting the measurement may shift during that time. For example, the earth's magnetic field is responsible for part of the signal and its value changes during the day due to the changing state of the ionosphere and to the contribution of the magnetic field of the sun. Another complicating factor is that the primary current may change through instabilities in the output voltage of the power supply, changes in the contact resistance of the leads, and temperature induced changes in the resistance of the primary winding itself as the equilibrium temperature varies. Also, changes in the physical position of the sensor can alter its output due to the presence of magnetically active objects in the vicinity and to changes of its position relative to the direction of the earth's magnetic field. The approach taken in this measurement to eliminate the signal noise introduced by all these factors is to measure the sensor response in air not just once before the measurement but before every data point, with as little time in between as possible. In this way every measurement data point has its own air calibration reference.

TABLE 5

Permeability/Lift-off measurement results corresponding to FIG. 13.

| Data Set | Relative Permeability | Lift-off [mm] | Nominal Lift-off [mm] |
|---|---|---|---|
| 1 | 4.23 | 3.3 | 3.3 |
| 2 | 4.30 | 4.1 | 4.1 |
| 3 | 4.30 | 4.8 | 4.8 |
| 4 | 4.29 | 5.7 | 5.6 |
| 5 | 4.28 | 6.6 | 6.5 |
| 6 | 4.19 | 7.2 | 7.3 |
| 7 | 4.21 | 8.0 | 8.0 |
| 8 | 4.36 | 9.1 | 8.8 |
| 9 | 4.37 | 9.9 | 9.4 |
| 10 | 4.39 | 10.8 | 10.2 |
| 11 | 4.21 | 11.1 | 10.9 |
| 12 | 4.28 | 12.2 | 11.7 |
| 13 | 4.43 | 13.5 | 12.6 |
| 14 | 4.44 | 14.3 | 13.4 |
| 15 | 4.41 | 14.9 | 14.1 |
| 16 | 4.50 | 16.1 | 14.9 |

Despite the limitations associated with performing DC measurements, the results in Table 5 are still good. The lift-off tracks the nominal lift-off values, but not as well as the data of Table 4. The relative permeability of the polymer layer is measured to be about 4.3 and the data follow a constant permeability curve quite well. As in the conductivity/lift-off measurements of Table 4, the measurement results are most accurate for lift-off values in the 5–7 mm range. It is also noteworthy that the, in FIG. 13, that at the highest lift-off values, there is a range where the magnitude of the short wavelength signal is lower than that of air. The grid lines confirm that this effect is physical. It is due to the fact that far away from the surface the magnetizable layer is too distant to intercept any magnetic field lines going through the center of the sensor but is still sufficiently close to attract some of the field lines away from the surface. An exact dual of this effect is observed in the dielectrometer grids in the presence of a ground plane behind the material sample.

Many applications often require the measurement of the thickness of a metallic coating on a metal substrate. One typical multi-layer structure has at least three layers, two metal layers and an air layer, where the conductivity and magnetic permeability of the two metal layers are known. Low frequency operation, made possible by the GMR eddy current sensor, will allow measurement of much higher coating thicknesses than existing spatially periodic field eddy current sensors.

Figure 14:
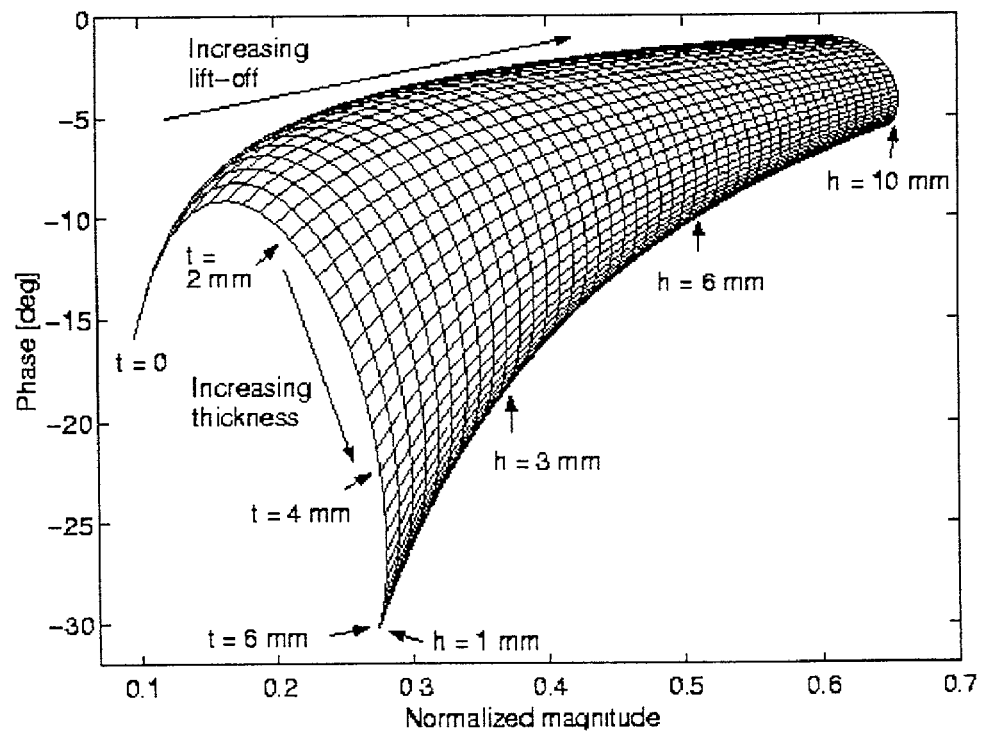
FIG. 14 shows a thickness/lift-off measurement grid for the circular magnetometer at 12.6 kHz. The thickness is of a stainless steel layer on an infinitely thick copper substrate.

The measurement grid used in this application is shown in FIG. 14, which assumes a stainless steel layer is on an infinitely thick copper substrate. Note that a material can be considered infinitely thick when the thickness is several times larger than the depth of penetration of the magnetic field into the material. For generating the grid, the conductivity of the stainless steel was taken as 1.39 MS/m and the conductivity of the copper was taken as 58 MS/m. The copper plate is 3.2 mm thick, but is modeled as infinite, since it is several times greater than the value of the skin depth of copper at this frequency (0.59 mm). In comparison, due to its much lower conductivity, the skin depth in the stainless steel layer (3.8 mm) is several times greater than that of the copper layer, and comparable to the plate thickness. By considering the size of the grid cells, it can be observed that the thickness measurement (but not the lift-off) loses sensitivity for thickness values below about 0.5 mm and above 5 mm. This is explained by comparing these values to the skin depth of 3.8 mm. At the lower thickness values the stainless steel layer has little influence on the magnetic fields, since its conductivity is much lower than that of the copper layer, which dominates the sensor response. At the high end of the thickness range the exponential decay of the magnetic field intensity makes the sensor insensitive to the position of the interface between the stainless steel and the copper. For these two limits the grid lines asymptotically approach two constant lift-off lines of the infinite-half-space conductivity/lift-off rid in FIG. 10, corresponding to the conductivities of copper and stainless steel. Optimal sensitivity, corresponding to the most open and orthogonal grid cells, is achieved for thicknesses on the order of 3 mm, close to $\delta\pi/4$.

Figure 15:
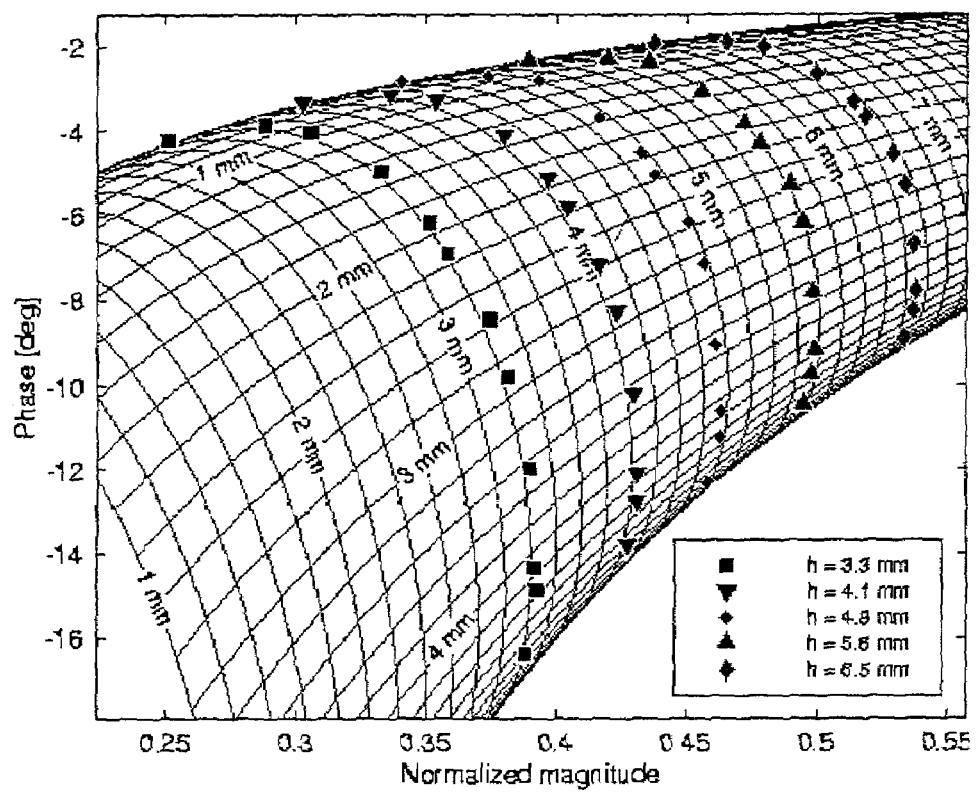
FIG. 15 shows the results of a stainless steel layer thickness measurement at five different lift-offs.

The thickness of the stainless steel layer in this set of measurements was changed by stacking up to four plates of various thicknesses in different combinations. Twelve sets of data were taken at each of five different lift-off values. The results are shown in FIG. 15 and listed in Table 6. Excellent agreement between the nominal and estimated values of thickness and lift-off was obtained, which confirmed the validity of the analytical model including representation of field interaction with a multiple layered material under test. Higher frequency measurements would improve the sensitivity to the thickness of thinner coatings by reducing the skin depth.

TABLE 6

Coating thickness estimation results corresponding to the data of FIG. 15.

| Data Set | h = 3.3 mm | | h = 4.1 mm | | h = 4.8 mm | | h = 5.6 mm | | h = 6.5 mm | | Nominal |
|---|---|---|---|---|---|---|---|---|---|---|---|
| | Thk. | Lift. | Thk. | Lift. | Thk. | Lift. | Thk. | Lift. | Thk. | Lift. | Thick. |
| 1 | −0.33 | 3.57 | −0.33 | 4.40 | −0.33 | 5.05 | 0.02 | 5.60 | 0.24 | 6.33 | 0.00 |
| 2 | 0.61 | 3.26 | 0.63 | 4.06 | 0.63 | 4.72 | 0.71 | 5.54 | 0.69 | 6.49 | 0.60 |
| 3 | 0.92 | 3.26 | 0.93 | 4.09 | 0.94 | 4.81 | 0.94 | 5.64 | 0.97 | 6.54 | 0.96 |
| 4 | 1.49 | 3.23 | 1.50 | 4.08 | 1.56 | 4.73 | 1.53 | 5.57 | 1.55 | 6.51 | 1.50 |
| 5 | 1.93 | 3.23 | 1.94 | 4.07 | 1.95 | 4.76 | 1.95 | 5.60 | 1.97 | 6.53 | 1.89 |

TABLE 6-continued

Coating thickness estimation results corresponding to the data of FIG. 15.

| Data Set | h = 3.3 mm Thk. | Lift. | h = 4.1 mm Thk. | Lift. | h = 4.8 mm Thk. | Lift. | h = 5.6 mm Thk. | Lift. | h = 6.5 mm Thk. | Lift. | Nominal Thick. |
|---|---|---|---|---|---|---|---|---|---|---|---|
| 6 | 2.14 | 3.21 | 2.16 | 4.06 | 2.16 | 4.73 | 2.15 | 5.60 | 2.16 | 6.51 | 2.10 |
| 7 | 2.57 | 3.25 | 2.58 | 4.06 | 2.56 | 4.78 | 2.56 | 5.63 | 2.57 | 6.54 | 2.49 |
| 8 | 2.9 | 3.24 | 2.90 | 4.06 | 2.88 | 4.77 | 2.89 | 5.60 | 2.90 | 6.53 | 2.85 |
| 9 | 3.45 | 3.24 | 3.47 | 4.05 | 3.50 | 4.72 | 3.50 | 5.55 | 3.52 | 6.49 | 3.39 |
| 10 | 4.13 | 3.22 | 4.12 | 4.04 | 4.13 | 4.75 | 4.13 | 5.55 | 4.10 | 6.50 | 3.99 |
| 11 | 4.33 | 3.24 | 4.43 | 4.06 | 4.46 | 4.75 | 4.46 | 5.55 | 4.44 | 6.49 | 4.35 |
| 12 | 5.03 | 3.23 | 5.01 | 4.05 | 5.30 | 4.76 | 5.04 | 5.55 | 5.04 | 6.49 | 4.95 |

Another example application is thickness measurements of relatively thick aluminum plates, where the thickness can be 0.25 inches or greater. This requires the use of low excitation frequencies, such as 100 Hz, where the skin depth is 9.5 mm in aluminum. One important application of this type of measurement is corrosion mapping, where the surface that corrodes is often not accessible for direct measurement. Since the other material property being measured is conductivity, a scan of this type would simultaneously detect cracks and other flaws in the metal. Also, multiple frequency methods could be added to vary the field depth of penetration.

Figure 16:
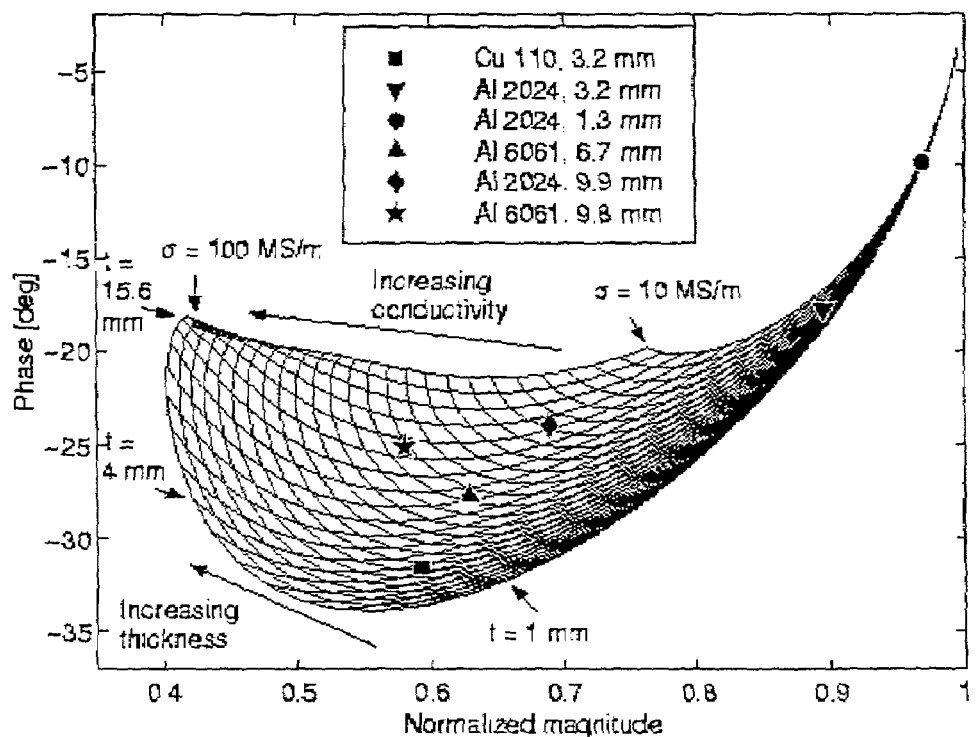
FIG. 16 shows a low frequency 100 Hz conductivity/thickness measurement grid and results for six metal plates.

The conductivity/thickness grid used in this set of measurements is shown in FIG. 16. In this case, this grid does not have lift-off as one of the two estimated parameters. The lift-off is assumed to be known and equal to 3.3 mm, the intrinsic magnetometer value obtained from earlier measurements. There are two reasons why lift-off is almost always one of the unknown properties in magnetometer measurements: (1) the lift-off is usually not known, because at the lower thickness scales typical of eddy current sensors, dust particles and surface roughness make a non-negligible contribution; and (2) grids including lift-off have more closely "orthogonal" cells, as other material properties are less independent of each other when they enter the model. The relatively large minimum lift-off value for this sensor reduces the importance of the first consideration. The second consideration still remains as an issue, as can be observed in the upper right corner of the grid where the grid cells collapse and approach zero area, as their edges become almost parallel to each other. Grid look-ups in such an area of the grid are naturally unreliable. Nonetheless, there is a big area of the grid where the two unknown properties are sufficiently independent of each other.

Figure 17:
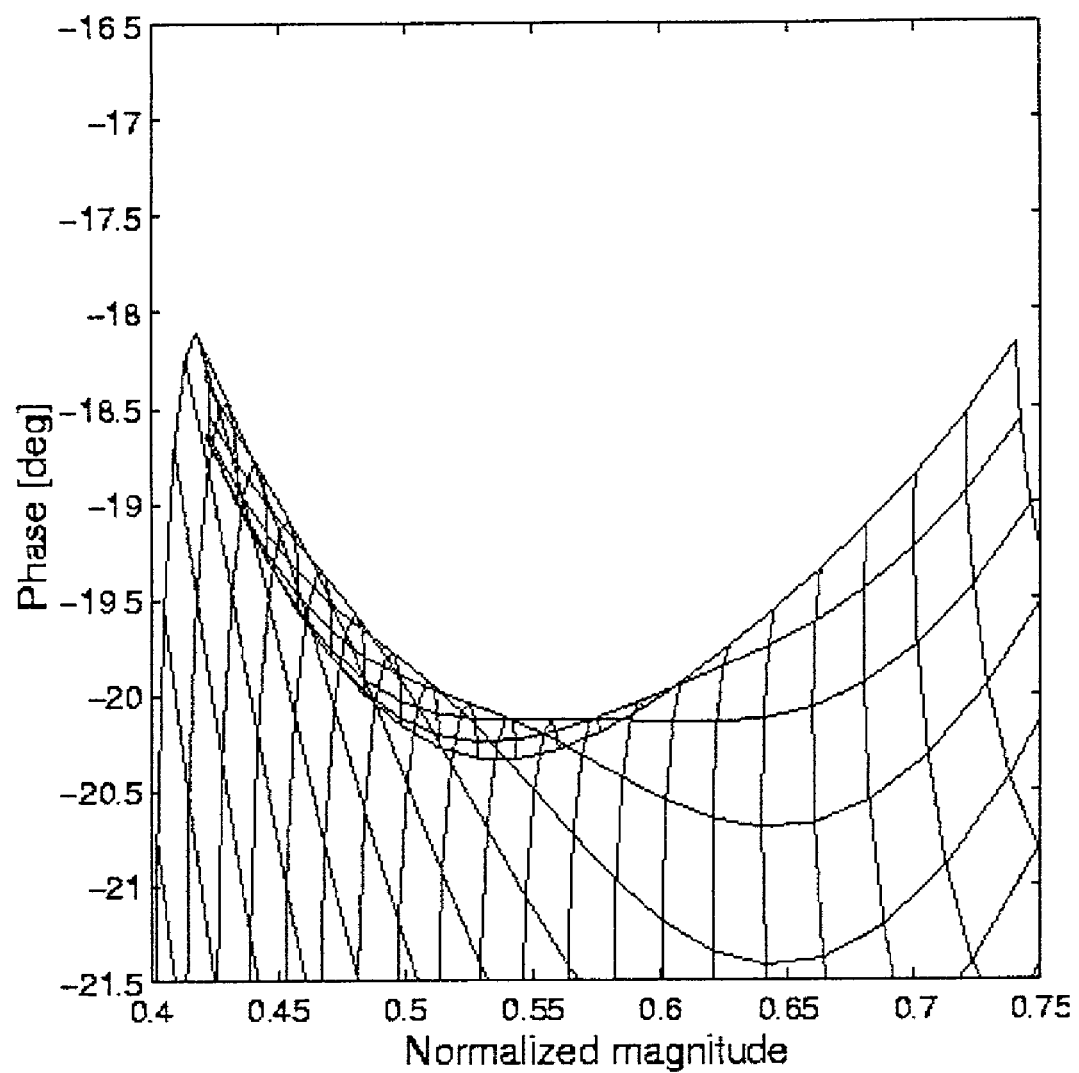
FIG. 17 shows an expanded view of the upper left corner of the grid in FIG. 16, illustrating the curl in the grid.
Figure 18:
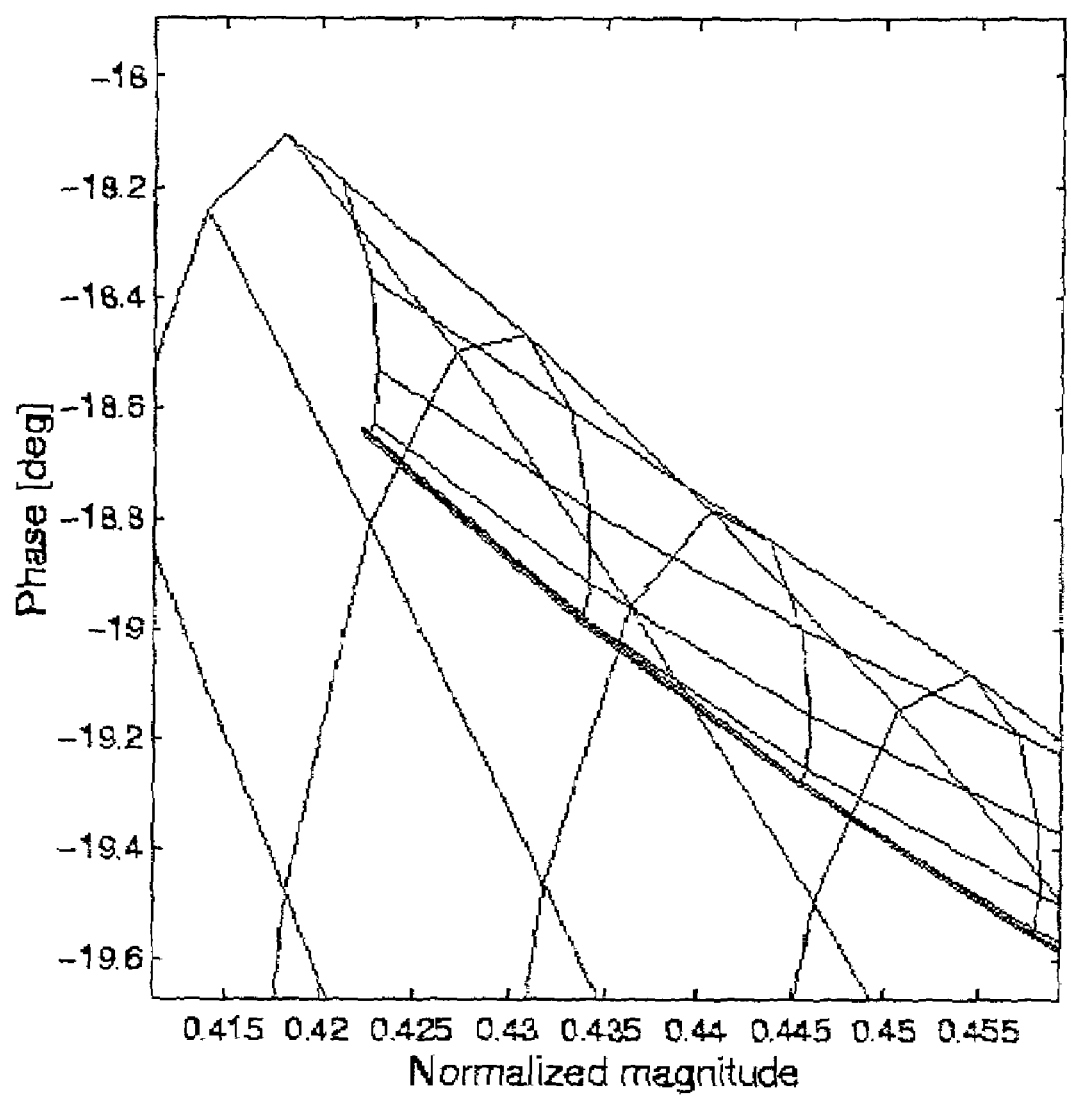
FIG. 18 shows a further expanded view of the curl in the upper left corner of the grid in FIG. 16.

An interesting property displayed by the grid of FIG. 16 is that near the upper left corner, lines of constant conductivity form spirals as they approach the limiting point corresponding to infinite thickness. As a result, the grid folds in on itself, sometimes several times for a large range of thicknesses. This means that for certain values of the complex sensor magnitude there can be two or more solutions, all physically valid. Expanded views of this region of the grid are shown in FIG. 17 and FIG. 18. The grids can manifest this kind of behavior when one of the unknown parameters is the thickness of the metal layer. This is caused by the fact that in the presence of magnetic diffusion, the exponent of the z-dependent term is a complex number and, due to the imaginary part of the exponent, the phase of the induced eddy currents changes with depth. As a result, the missing tail of the exponent, due to the finite width of the layer, can alternatively enhance or reduce the fields at the secondary sensor, leading to the spiral grid effect. This effect has been observed for other deep penetration eddy current sensors such as the magneto-optical imaging (MOI). This behavior is analogous to the evanescent decay of standing waves of electromagnetic field in high frequency (e.g., microwave or optical) systems such as transmission lines or the reflection and transmission of plane waves at interfaces.

The thick plate measurement results, listed in Table 7, show good agreement with the conductivity values in the literature and the nominal thicknesses measured with a caliper. One notable exception is the 1.3 mm thick aluminum plate. This plate thickness is simply out of the range of sensitivity for this measurement, as can be seen visually in FIG. 16, where this point falls in a very narrow region of the grid. Similarly, the 2024 Al 3.2 mm point is also in a very narrow region, but actually resulted in a good thickness and conductivity estimate for this example.

TABLE 7

Low frequency (100 Hz) conductivity/thickness measurement results corresponding to the data of FIG. 16.

| Data Set | Material | Nominal Conductivity [MS/m] | Nominal Thickness [mm] | Measured Conductivity [MS/m] | Measured Thickness [mm] |
|---|---|---|---|---|---|
| 1 | Cu 110 | 58.0 | 3.2 | 56.2 | 3.39 |
| 2 | Al 2024 | 17.5 | 3.2 | 17.5 | 3.34 |
| 3 | Al 2024 | 17.5 | 1.3 | 12.5 | 2.19 |
| 4 | Al 6061 | 27.3 | 6.7 | 29.1 | 6.53 |
| 5 | Al 2024 | 17.5 | 9.9 | 17.1 | 10.38 |
| 6 | Al 6061 | 27.3 | 9.8 | 28.1 | 9.52 |

Another set of measurements illustrates the GMR magnetometer capability to detect material flaws in a thick layer of metal. These measurements were carried out by performing scans over a set of stainless steel plates. One plate had a 25 mm long, 0.4 mm wide, and 2.4 mm depth slot to simulate a crack. The grid used for this measurement is the conductivity/lift-off grid in FIG. 10. The crack is not modeled explicitly, but its presence is usually manifested by a local reduction in the value of the measured conductivity. In some cases, depending on its depth and position below the surface, it may appear as a local change in the lift-off.

Figure 19:
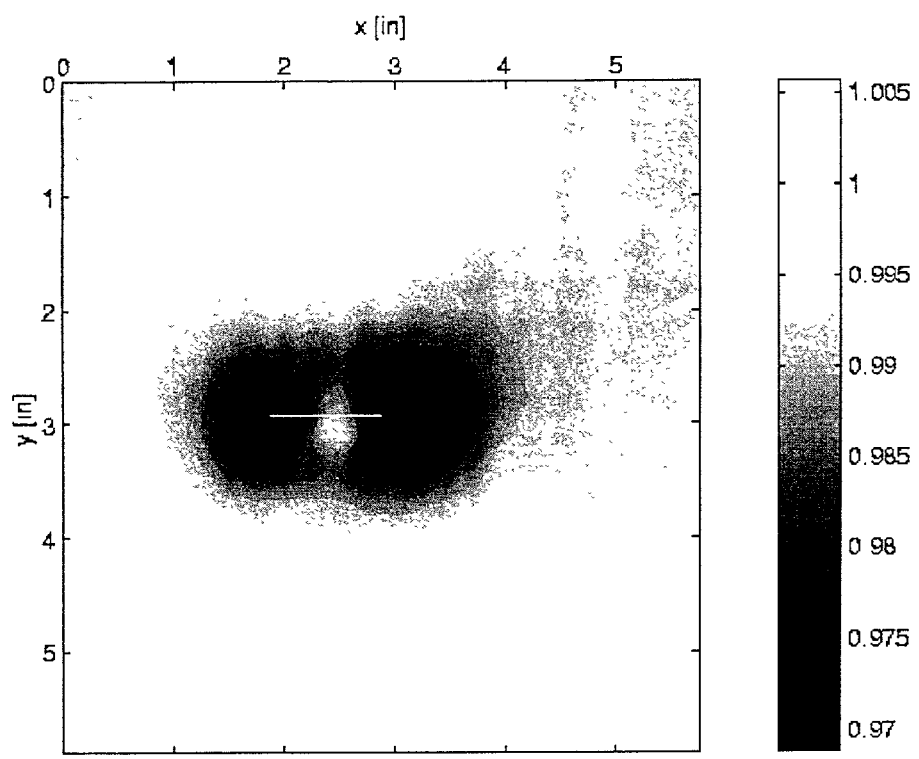
FIG. 19 shows an area scan of a stainless steel plate with the crack at the surface.

Three sets of scans were made with stainless steel plates arranged to simulate a crack at the upper surface, nearest the sensor, a crack 3.2 mm below the upper surface, and a crack 7.2 mm below the surface. The image generated by the first scan, with the slot at the surface, is shown in FIG. 19. This image shows the conductivity, normalized by its value away from the crack. The crack signal is very strong, with the conductivity decreasing more than 3% near the crack position. The double hump signature of the crack is characteristic of the effect cracks have on the signal of imposed-periodicity eddy current sensors. The induced current density mirrors the current density of the drive, and as a consequence, the disruption caused by the crack is greatest when it is directly below, and perpendicular, to the primary winding nearest to the sensing element.

Figure 20:
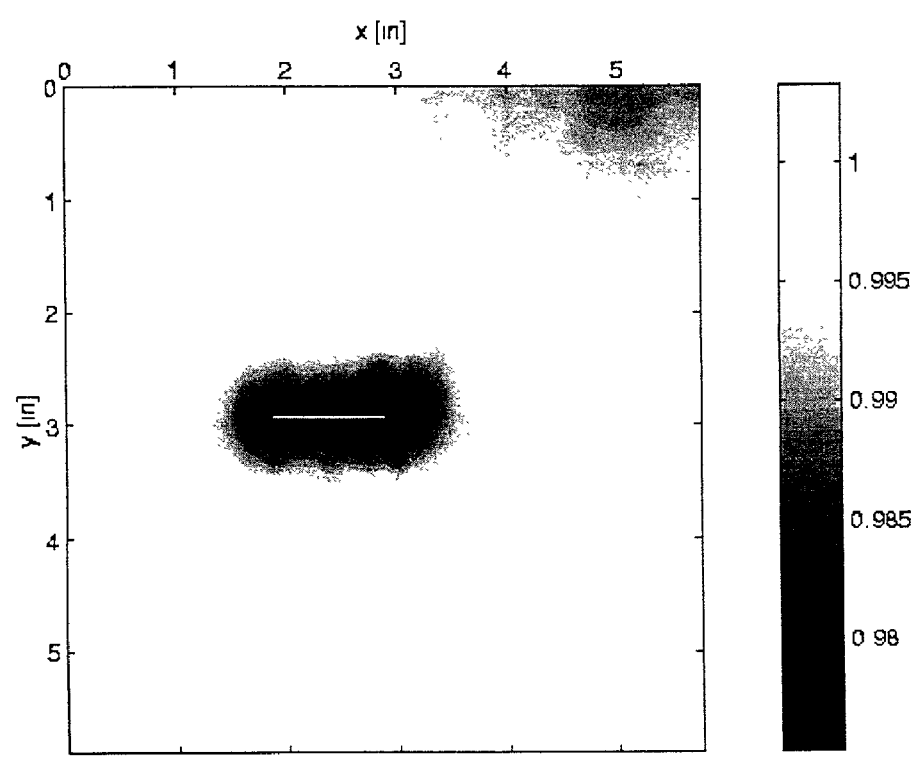
FIG. 20 shows an area scan of a stainless steel plate with crack 3.2 mm below the surface, The position of the crack being indicated with a white line.

The conductivity image generated with the crack positioned 3.2 mm below the surface is shown in FIG. 20. The change of the effective conductivity is approximately 2.5%. The image generated with the crack 7.2 mm below the surface is shown below in FIG. 21. In this case, the conductivity change was less than 0.5%, which is only slightly above the noise level. This is to be expected, since the skin depth of stainless steel at this excitation frequency is 3.8 mm. The quality of the image at this depth can be improved by measuring at a lower frequency.

Figure 21:
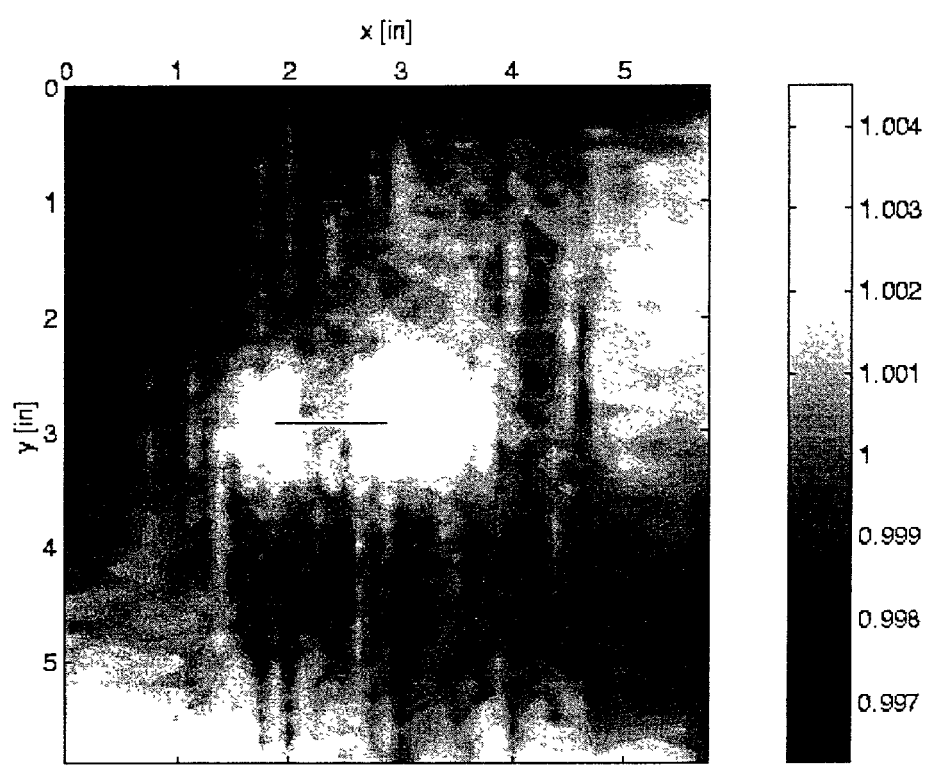
FIG. 21 shows an area scan of a stainless steel plate with crack 7.2 mm below the surface. The position of the crack is indicated with a black line. Because of the change in phase of the induced current, at this depth the polarity of the crack signature is reversed

An interesting feature to be observed in FIG. 21 is that near the crack, the measured conductivity is actually higher. This is because the phase of the induced eddy currents changes with depth and is also what causes the grid in FIG. 16 to curl inwards. With the crack positioned 7.2 mm below the surface it interrupts eddy currents that are flowing in a direction opposite to the surface eddy currents, thereby increasing the magnetic field at the sensor. A consequence of this effect is that there is a characteristic depth, near $\pi/2$ skin depths, where a crack would cause no change in the conductivity. For this reason, it is common practice to test at more than one frequency. This is not as troublesome as it may seem, for while the real part of the exponent may be zero, at this characteristic depth the imaginary component is not, and therefore the crack signature would show up in a plot of the lift-off. This is also evident in the grid in FIG. 16, where a constant conductivity line may change its direction along a spiral, but never crosses itself.

Figure 22:
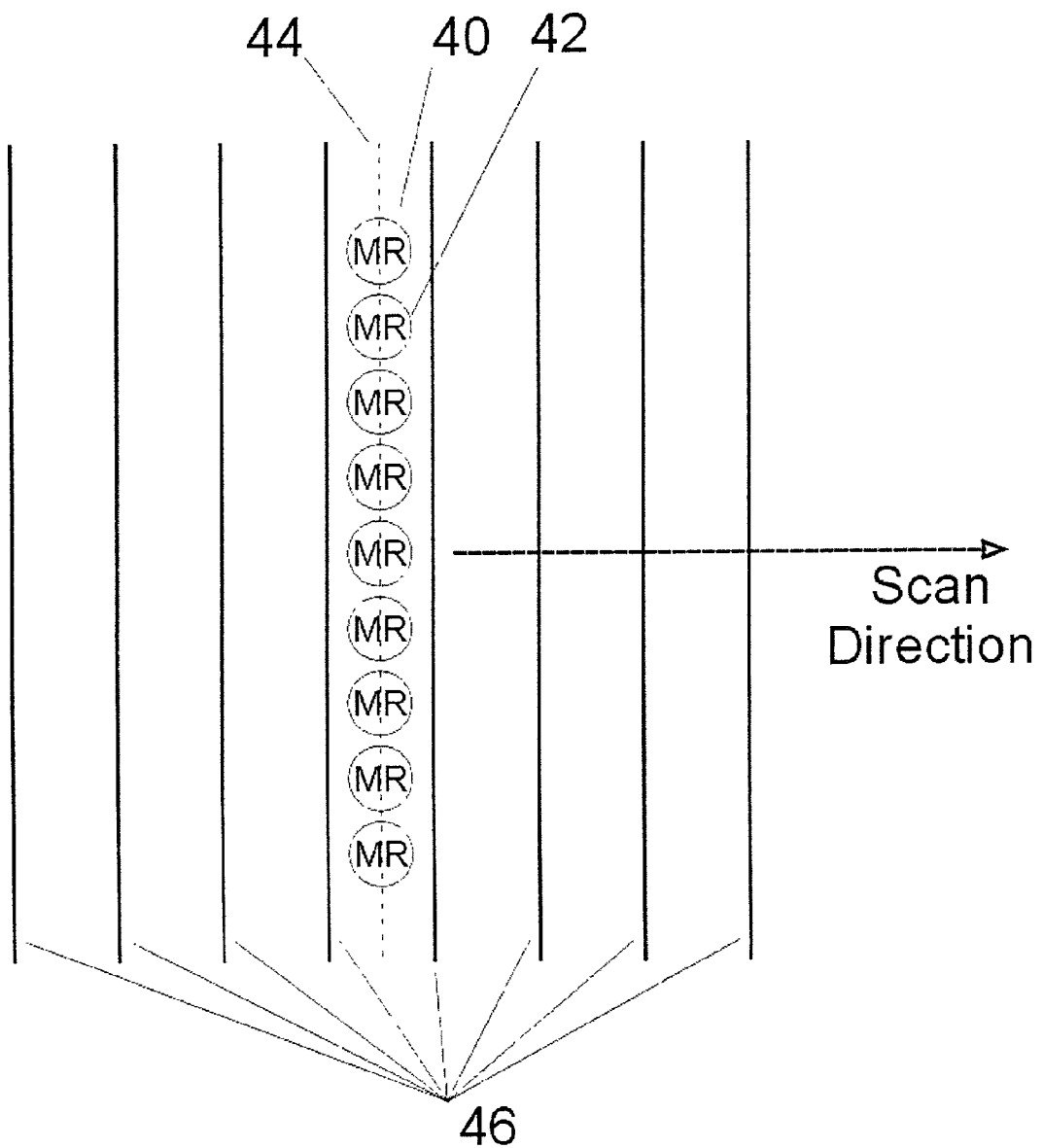
FIG. 22 shows a linear array of sense elements across drive windings having Cartesian geometry.
Figure 23:
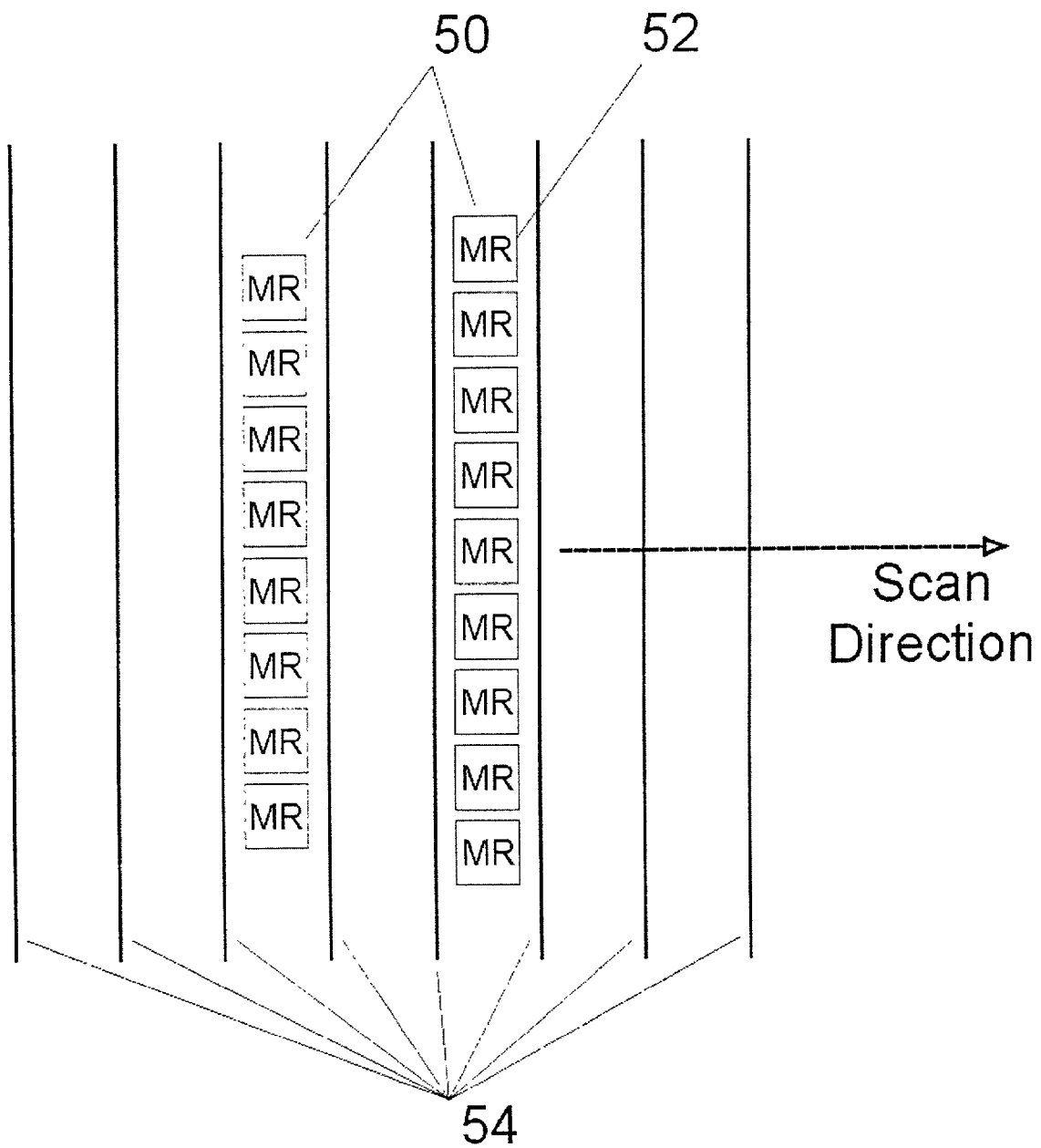
FIG. 23 shows a pair of linear arrays of sense elements across drive windings having Cartesian geometry.
Figure 24:
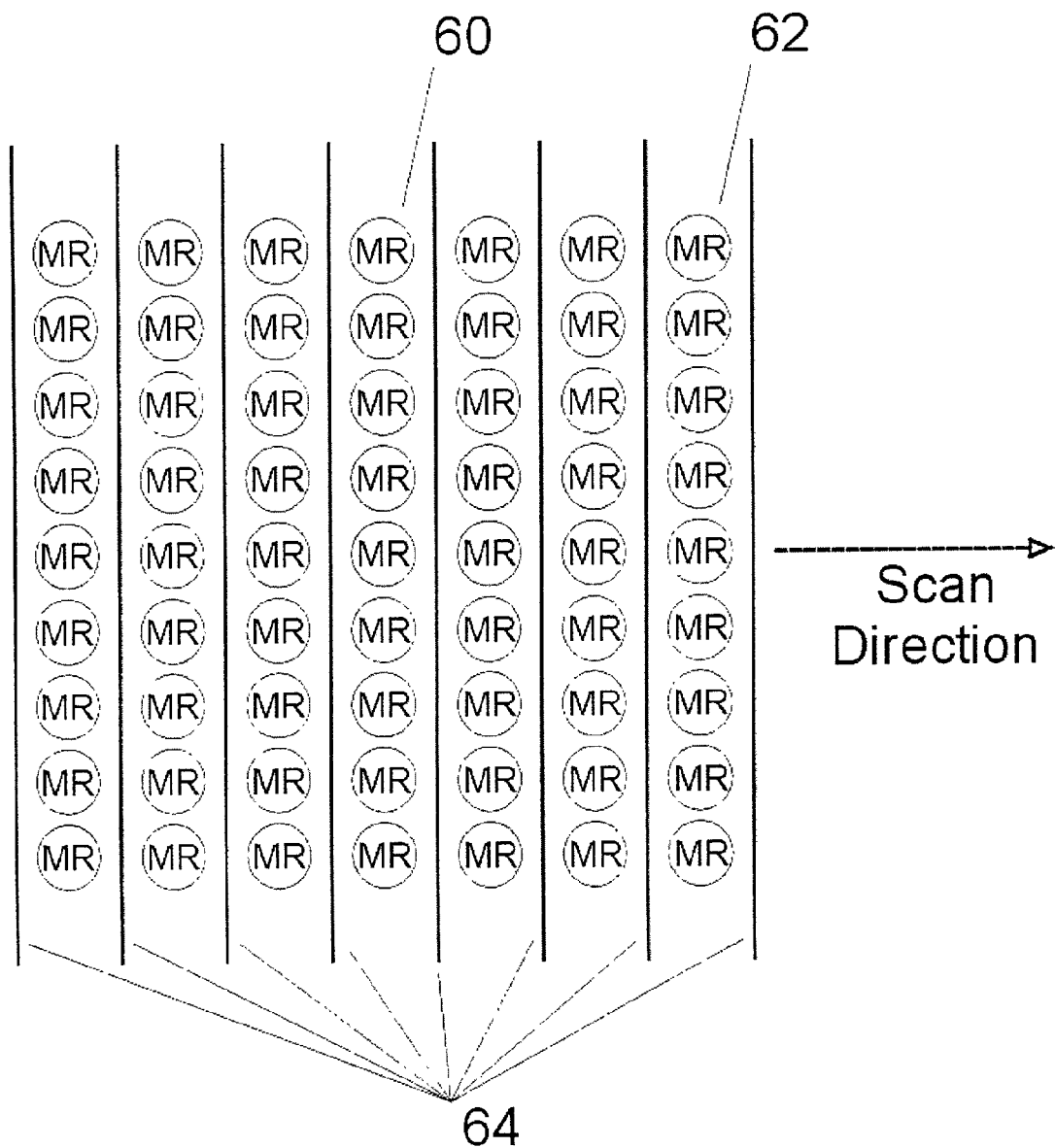
FIG. 24 shows an areal array of sense elements across drive windings having Cartesian geometry.

A variety of other adaptations for the device design are also available. When the goal is to discriminate between near-surface and deep material properties, multiple sensing elements can be placed across the footprint of the array. These arrays can incorporate giant magnetoresistive sensor elements. FIG. 22 shows a linear array 40 of sensing elements 42 placed along the centerline 44 of a Cartesian array of drive winding segments 46. The linear array is perpendicular to the scan direction to facilitate the construction of images of the measured material properties. FIG. 23 shows a pair of linear arrays 50 of sensing elements 52 within the footprint of a Cartesian array of drive winding segments 54. In this case, the elements in each array are offset in the direction perpendicular to the scan direction by half the element dimension. This provides overlap in the measurement images created by each sensing element so that small flaws and defects cannot fall between the sensing elements when the sensor is scanned over the test material. FIG. 24 shows a two-dimensional array 60 of sensing elements 62 placed throughout the footprint of the drive winding segments 64. Note that the drive winding segments 46 (FIG. 22), 54 (FIG. 23), and 64 (FIG. 24) of each respective embodiment are connected together with side connections, similar to the side connections 20 shown in FIG. 4, to maintain the continuity of current through the drive winding segments.

Figure 25:
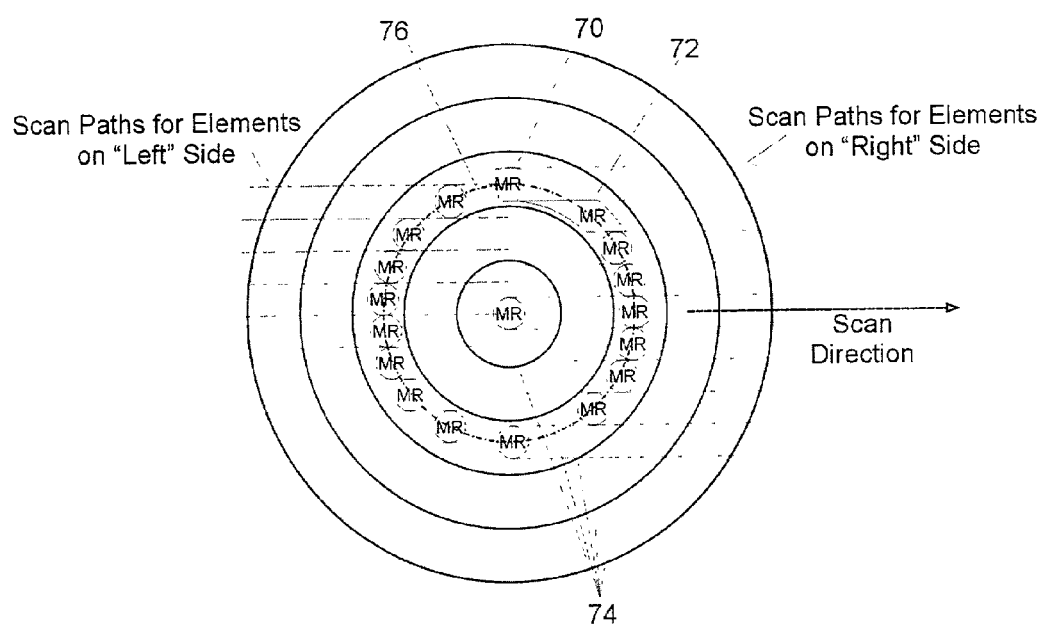
FIG. 25 contains a circular array of sense elements around drive windings having a rotationally symmetric geometry.

FIG. 25 shows a circular array 70 of sensing elements 72 placed around the circumference of a drive winding 74 having rotational symmetry. Interconnections between each segment of the drive winding 74 are made with conductor pairs similar to the conductor pairs 32 shown in FIG. 5. The locations of the sensing elements around the circumference of the center line 76 are staggered so that the effective scan paths for the sensing elements on the right and left sides of the sensor will overlap when the sensor is scanned over the test material. The sensor elements may be run with or without feedback loops and may be placed on a flexible support structure. The feedback secondary coils can take a variety of shapes, such as circular (FIG. 22) or square (FIG. 23). For biasing, a permanently magnetized flexible layer may be used. In addition, a magnetizable layer on the front or back of the sensor can also be used to shape the magnetic field and/or improve sensitivity to property variations.

Figure 26:
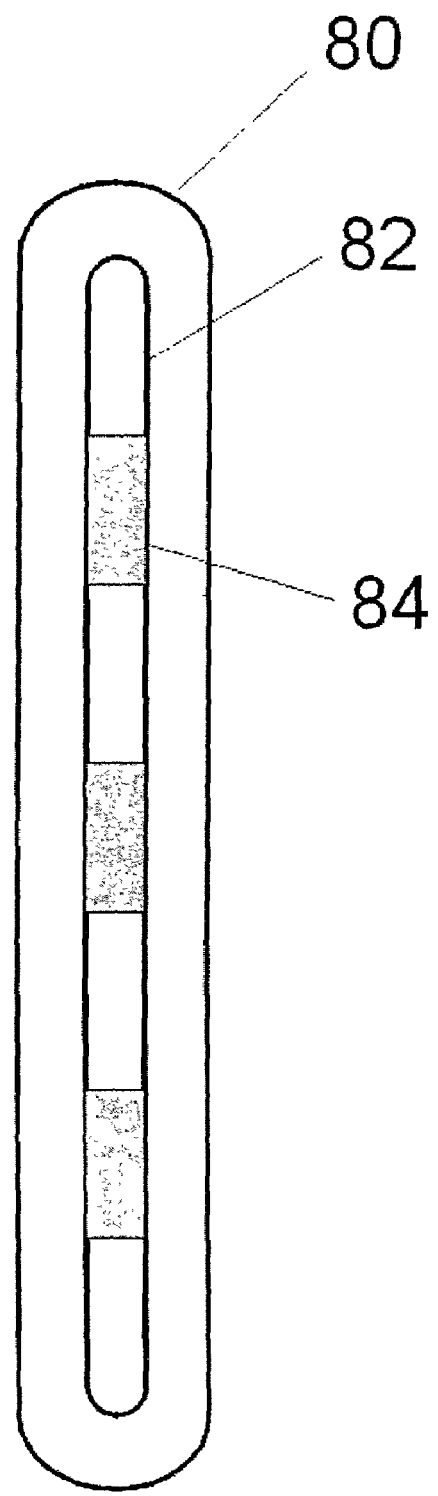
FIG. 26 shows multiple GMR sensors placed within a feedback coil and at the center of a drive winding.
Figure 27:
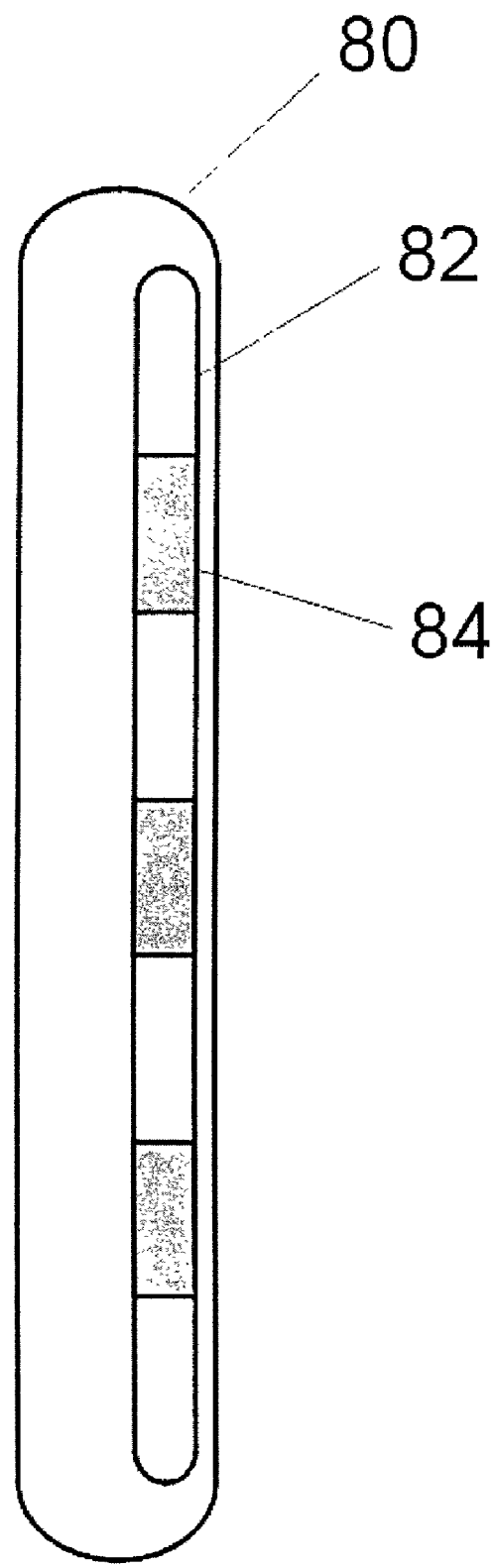
FIG. 27 shows multiple GMR sensors placed within a feedback coil and offset near an edge of a drive winding.
Figure 28:
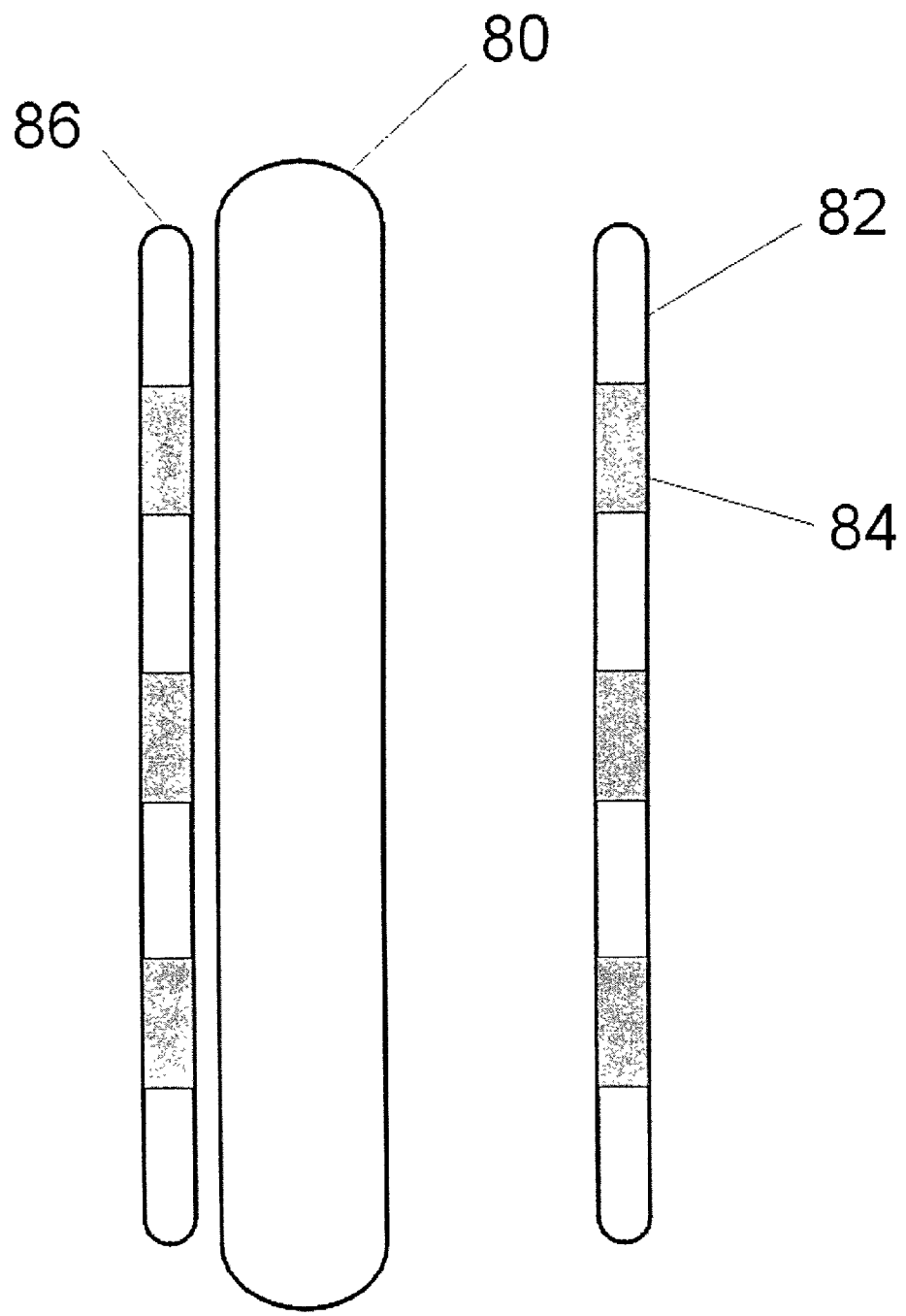
FIG. 28 shows two linear arrays of GMR sensors placed within feedback coils and external to the drive winding.
Figure 29:
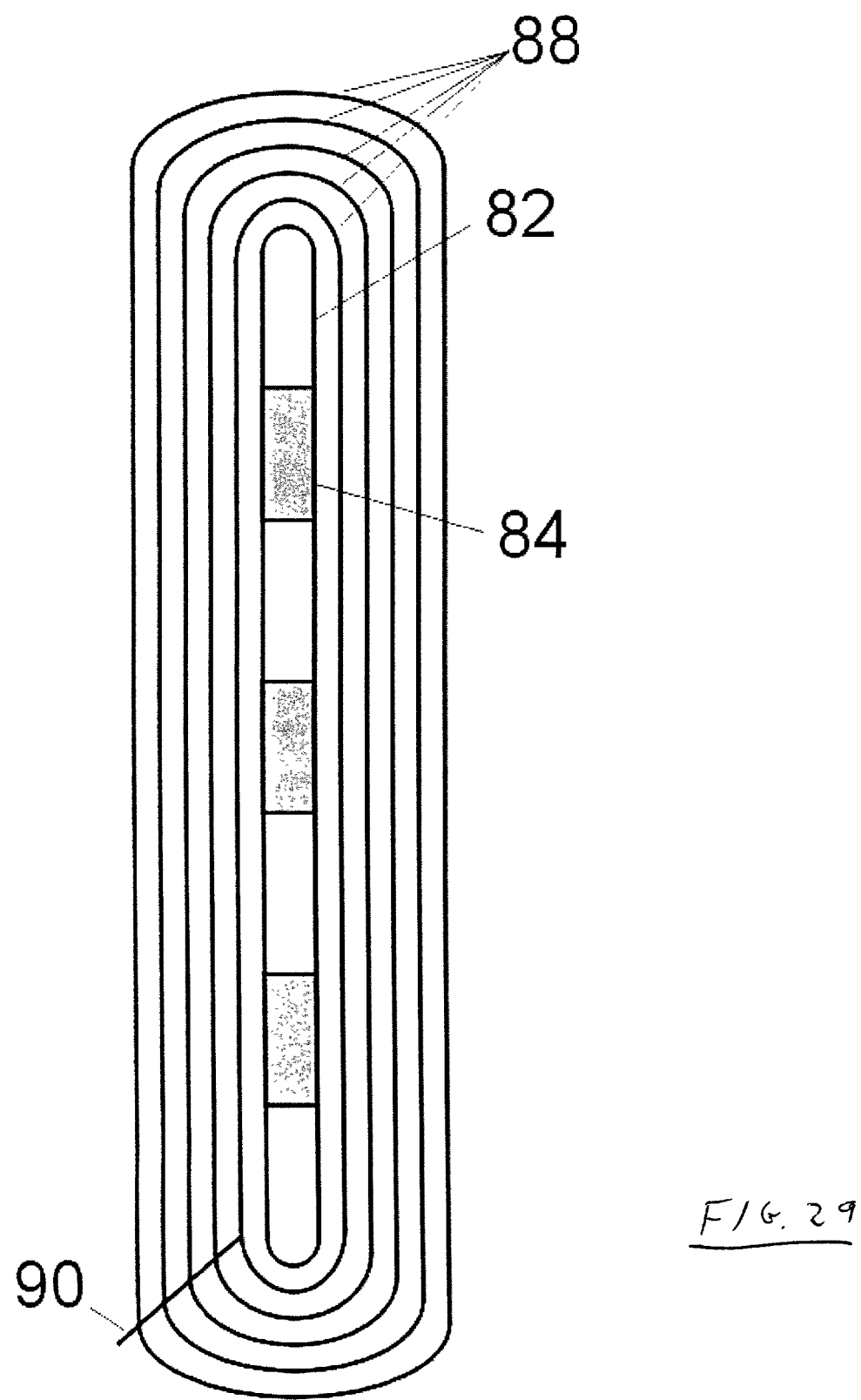
FIG. 29 shows multiple GMR sensors placed within a feedback coil and at the center of a shaped field distributed drive winding.

The position of the GMR elements within the feedback coil, and the position of the feedback coil within the primary winding can also be adjusted. FIG. 26 illustrates that one or more GMR sensors 84 can be surrounded by a feedback coil 82 and placed at the center of a drive winding 80. The use of multiple GMR sensors within the footprint of the drive winding promotes imaging of material properties when the array is scanned in a direction perpendicular to the row of GMR sensors. The use of a single feedback coil and multiple GMR sensor elements eliminates cross-talk between elements, which may occur if each GMR element has its own feedback coil, and also simplifies the drive circuitry for the sensor array. FIG. 27 shows a similar array with the row of GMR elements 84 and feedback coil offset so that it is closer one side of the primary winding than the other. This results in an asymmetric response when the array is scanned over a flaw since the array is more sensitive to the effects of the flaw when it passes beneath the nearer portion of the primary winding. Similarly, sensing elements can be placed outside of the drive winding, as illustrated in FIG. 28, where the row of sensor elements 84 is far from the drive winding 80 while a second row of sensors 86 is near the drive winding. An advantage of this configuration is that any connection leads to the sensing elements does not have to pass over the conductors of the drive winding, which helps to minimize parasitic responses. FIG. 29 shows a similar configuration with a shaped field or distributed winding structure. The drive winding contains multiple conductor segments 88 for imposing the magnetic field while one or more GMR sensors 84 are placed within a feedback coil 82 within the drive structure. The connection to a drive winding conductor 90 also shows that each of the drive winding conductor segments 88 are interconnected. As with the single winding drives, the GMR sensors do not need to be placed at the center of the distributed drive structure.

The selection of the meandering or distributed single wavelength or half-wavelength (e.g., simple rectangle) winding design will vary depending on the depth of sensitivity required in a specific application and access issues for the sensor. For some of these design considerations, refer to U.S. Pat. Nos. 5,015,951, 5,453,689, and 5,793,206. For example, detection of cracks under fastener heads should consider the fastener head size, the spacing of the fasteners, and the location of the sensing elements and drives relative to the fasteners, to maximize sensitivity and minimize interferences. Also, the type of defect, such as corrosion versus fatigue or residual stress, will affect the selection of the winding construct design.

Figure 30:
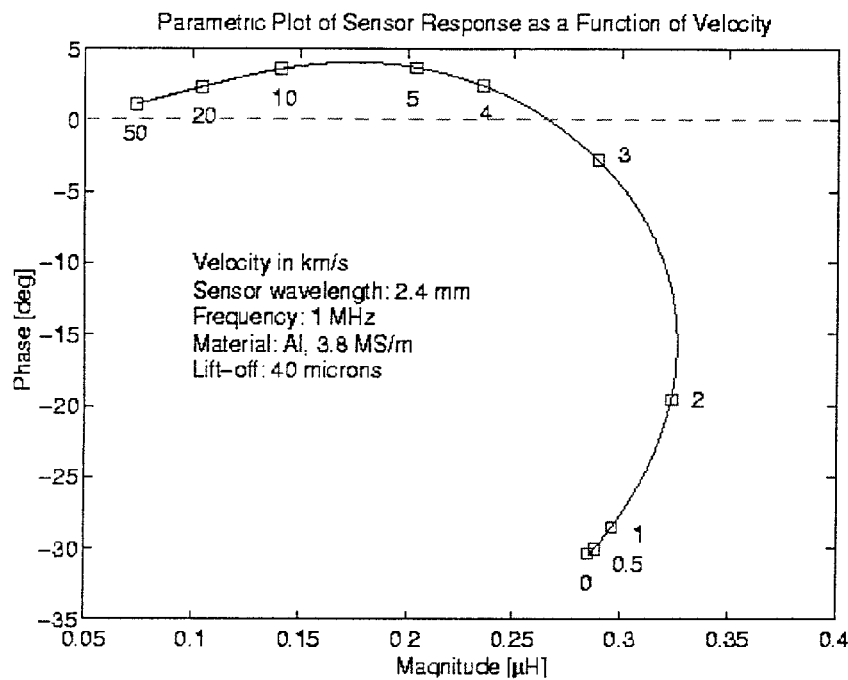
FIG. 30 shows a plot of the transinductance variation of a spatially periodic field eddy current sensor as the convection velocity is varied.
Figure 31:
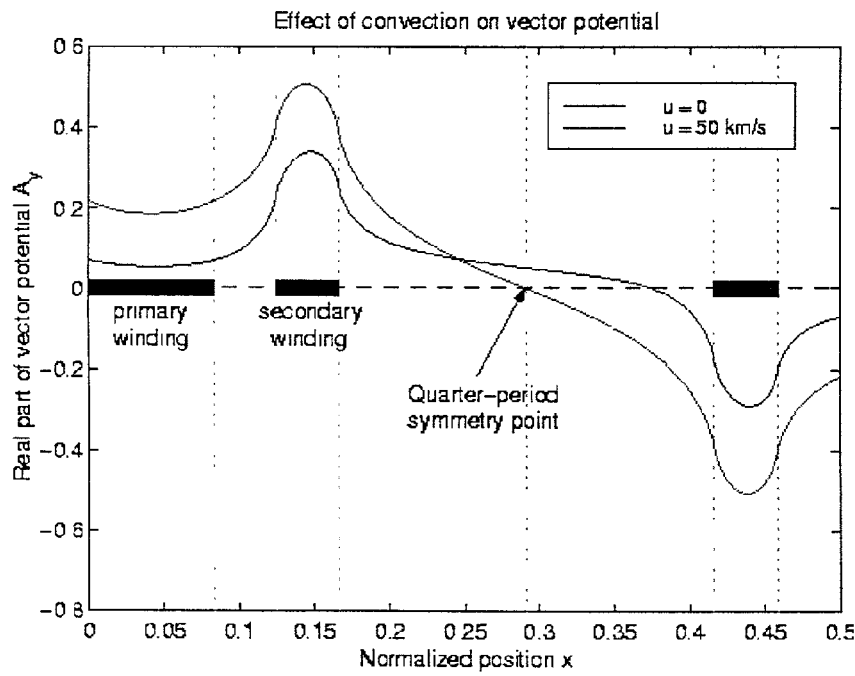
FIG. 31 shows a plot of the real part of the magnetic vector potential for stationary and moving media.

In many situations, the sensor or sensor array will be in motion relative to the test material. This can occur, for example, when scanning across the surface of a material for a flaw. Most often the time interval determined by the scanning speed and the characteristic length scale of the sensor is much greater than the time period of the imposed AC field, in which case the effects of the motion are negligible. However, in some situations the relative motion of the sensor and the material under test can influence the magnetic field distribution and the sensor response. For example, for a spatially periodic winding distribution and material motion in the same direction, then the magnetic vector decays exponentially with distance into a uniform material with a decay rate $$\gamma = \overline{\sqrt{k^2 + j\sigma\mu(\omega) - ku)}} \quad (1)$$

where $k=2\pi/\lambda$ is the wavenumber, $\sigma$ is the electrical conductivity, $\mu$ is the permeability, $\omega=2\pi f$ is the angular frequency of the excitation, and u is the material velocity. The velocity has the effect of changing the effective frequency of the excitation and hence the decay rate of the magnetic field into the material under test. This effect can be modeled and FIG. 30 illustrates how the sensor transinductance, shown on a magnitude/phase plot, changes as the material velocity is increased. One interesting result is that for a range of velocities the phase of the transinductance becomes positive, which corresponds to an impedance having a negative real component. This is not unphysical and is the result of the use of a single lumped element component representation for the two-port representation of a continuum system. Similar results have been observed with dielectric sensors yielded a negative transconductance. FIG. 31 shows a comparison in the magnetic vector potential between a moving and stationary metal layer. In addition to breaking the symmetry with respect to the quarter-period point, the motion also acts to decrease the magnitude of the potential. While the significance of the motion depends upon the excitation frequency, the fundamental spatial wavelength of the sensor, and the velocity, Eq. 1 suggests that low frequency measurements taken with high scan speeds (or velocities) may be impacted by the relative motion.

The real-time estimate of material or geometric properties requires the use of efficient table look-up and interpolation algorithms. These algorithms convert the value of the measured transimpedance of a sensor to material properties (parameter estimation) by interpolating between the points of a look-up table of pre-computed sensor responses (known as a measurement grid). The type of interpolation that needs to be carried out for a grid look-up is not what is done in typical look-up table algorithms, which are forward interpolation algorithms. This is a critical distinction. Interpolation methods of this nature are discussed in (Press, 1992), though the subject of two-dimensional inverse interpolation algorithms is not discussed.

The concept of inverse interpolation is best illustrated with an example. Suppose there is a function y(x) whose values $y_n$ are known at a set of points $x_n$. x is the independent variable and $x_n$ are chosen by the designer of the look-up table to span the anticipated function domain. The most common task is finding a value for y at a given value of x. This is one-dimensional forward interpolation and is very easy to carry out since it is known from the start which $x_n$ is closest to x.

Finding a value of x that corresponds to a given value of y in this same table is known as inverse interpolation. It is a much more difficult operation especially if y(x) is not a monotonic function. Furthermore the values of y may be repeated and may not be evenly spaced.

In two dimensions, the forward interpolation entails finding the value of a function $y(x_1, x_2)$ given $x_1$ and $x_2$ by interpolating in a two-dimensional table. This can be done via bilinear interpolation or its higher order variants. The key feature is that, as in the one-dimensional case, the closest point in the table and the table cell needed for the interpolation is known from the onset. The actual interpolation is also easy since the table is designed to form a rectangular grid. Two-dimensional inverse interpolation comes about when there is a table that lists the values of two functions, $y_1(x_1, x_2)$ and $y_2(x_1, x_2)$ at a set of predetermined values of the independent variables, forming a rectangular grid. The goal is to find the appropriate values for $x_1$ and $x_2$ where the functions $y_1$ and $y_2$ contain a pair of known values. This inverse task is much more complicated than the forward task. Some of the complications are (1) even when both $y_1$ and $y_2$ fall inside the ranges of the corresponding functions, there is no guarantee that a solution exists; (2) it is not known at the outset what the indices of $x_1$ and $x_2$ are for the point closest to the target; and (3) even if the cell in the table that should be used for interpolation is found, in general in $y_1$ and $y_2$ sp ace this cell is not rectangular and no standard interpolation formula can be applied.

The starting point for the inverse interpolation is the identification of the grid cell that contains the target point. One method for identifying the closest grid point (in order to establish which cell to use in the interpolation) is to calculate the distance to each point on the grid and pick the point with the smallest distance. This is very inefficient because it requires calculating the distance to each point in the grid for each table-up and can also give the wrong results for highly elongated or non-orthogonal cell boundaries. A more efficient method is to judiciously choose a starting point and search in a local region of the grid until the required grid cell is located. This can be implemented in the following procedure:

1. Choose a starting point. Initiating the search close to the target point can significantly improve the efficiency of the search. In general, this should be the cell used in the last look-up, because it is very likely that consecutive measurements lie close together on the grid. In fact in most cases the last cell used contains the current target point, so that this step often concludes the search. If this is the first look-up, a rough interpolation is done based on the four corners of the grid to estimate the indices of the starting point, using method identical to the one described below.
2. Zoom out. If the target point is not inside the current cell, increase the size of the area tested to 2×2, 4×4, etc. until either the current grid "square" (collection of cells being considered) contains the target point, or it reaches a predetermined limit or the size of the entire grid.
3. Move the grid square. If the grid square currently under consideration does not contain the target point, move to the next grid square of the current size in the direction toward the target point. Keep moving until one of the following three conditions occurs: (a) the target point falls inside the current square; (b) the square reaches the edge of the grid; (c) it cannot be determined which the correct direction to move is. This last condition can occur in special cases near singular points, near grid folds where the multiple grid cells contain the target point, or if the current grid square is not a convex quadrangle.
4. Zoom in. If the size of the current grid square is greater than a single grid cell, reduce it by a factor of two and go back to step 3. Otherwise, end the search.

If in the end the current grid cell contains the target point, the search was successful. Otherwise, the target point is most likely off the grid.

There can be cases when the search fails even if the target point is on the grid. This can happen if the grid is so curved that moving in a direction toward the target in the lane of the grid (magnitude/phase space) moves away from the correct cell in parameter space. These cases are handled by reverting to the "brute force" method of computing the distance to every point on the grid and finding the closest grid point to the target point. It is then used as the starting cell for a second run through the search algorithm. If in fact the target point is on the grid, this will find the correct cell with a very high likelihood. Most often, however, the first run has failed because the point is off the grid, so that if used every time a point is off the grid, this second search step takes a disproportionately longtime to run, which can create problems especially when performing real-time estimations. Whether to give up after the first try or attempt the long search method depends on the particular application.

In order to determine the direction to move in step 3 above, a formula (Eq. 3) is applied. This calculates the area of the triangles formed by each of the four sides of the grid square and the target point. The sign of the result is used to determine whether the target point lies inside the square, or else in which direction the square is to be moved. For example, if the target point is to the "right" of both the "left" and "right" sides of the square, it must be moved one over to the right, etc. The directions here are put in quotations, because the meanings of "right", "left", "top", and "bottom" depend on the direction of increasing parameter index number, and on whether the grid is "right-handed" or "left-handed", i.e. whether the axes in magnitude/phase space and parameter space have the same or opposite sense.

Figure 32:
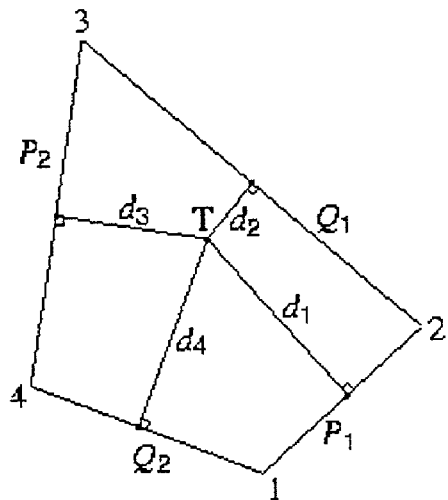
FIG. 32 shows a schematic diagram of a two-dimensional inverse interpolation within a grid cell.

After identifying the grid cell which contains the target point, the next step is to interpolate within the grid to determine the parameter values. A simple two-dimensional inverse interpolation is illustrated in FIG. 32. This interpolation method is based on the distances between the target point and the lines of constant parameter (P or Q):

$$P = \frac{d_3 P_1 - d_1 P_2}{d_3 - d_1} \quad Q = \frac{d_4 Q_1 - d_2 Q_2}{d_4 - d_2} \tag{2}$$

The distances $d_1$ through $d_4$ are calculated by dividing the area of the triangle with vertices at the two corners and the target point by the length of the cell side and then dividing by two. The following formulas is used to find the triangle area:

$$A_{ijk} = x_i(y_k - y_j) + x_j(y_i - y_k) + x_k(y_j - y_i) \tag{3}$$

The sign of $A_{ijk}$ is positive or negative, depending on whether the motion is in a positive (counterclockwise) or negative (clockwise) direction along the circumscribed circle when going from i to j to k. Therefore this formula retains directionality information although it calculates area. If all three points lie on a line, the result is zero. It is important to remember that the distances in Eq. 2 are signed quantities, so that when the target point lies inside the cell, $d_1$ and $d_3$ will have opposite signs, as do $d_2$ and $d_4$. The order of the area indices in Eq. 3 is important. The advantage of maintaining the polarity information is that the correct result will be obtained even if the target point lies outside the cell used for the interpolation.

The problem with this "simple" inverse interpolation method is continuity across cell boundaries. The value of the parameter associated with the cell wall being crossed, e.g., P when crossing line 1-2 in FIG. 32, will be continuous, because it is equal to the value of the parameter on that line ($P_i$). However, the value of the other parameter, e.g., Q when crossing line 1-2, will make a discontinuous jump as the grid cell being used for interpolation changes. This is usually a small jump since in most grids the walls of neighboring cells are nearly parallel. The practical implications of this discontinuous behavior are most pronounced when using iterative techniques to determine three or more unknowns where it could lead to lack of convergence. It is also possible to observe the effect when scanning along a part with continuously varying properties, using a coarse grid where the measured property may appear to change in step increments.

Figure 33:
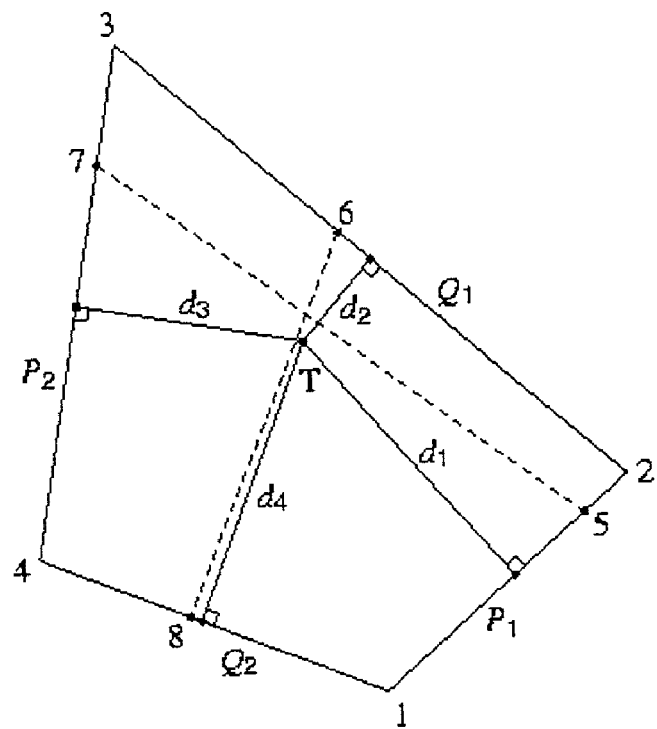
FIG. 33 shows a diagram of a grid cell and additional points in a complex two-dimensional inverse interpolation method.

A more complex inverse interpolation algorithm can be used to solve the discontinuity problem. This method relies on the fact that, given a target point on a grid cell wall, both of the estimated parameters, P and Q, must depend only on the coordinates of the target point and the two end points of the edge being crossed, common to both cells. For example, when the target point lies on line 1-2, both P and Q must depend only on the coordinates of points 1, 2, and T. With the simple method this is only true for P. This is accomplished using the method illustrated in FIG. 33. Instead of using Eq .2 to calculate P and Q directly, it is used to find the coordinates of four new points, 5-8, one on each of the four sides of the cell using:

$$x_5 = \frac{d_4 x_2 - d_2 x_1}{d_4 - d_2} \quad y_5 = \frac{d_4 y_2 - d_2 y_1}{d_4 - d_2} \tag{4}$$

$$x_6 = \frac{d_3 x_2 - d_1 x_3}{d_3 - d_1} \quad y_6 = \frac{d_3 y_2 - d_1 y_3}{d_3 - d_1}$$

$$x_7 = \frac{d_4 x_3 - d_2 x_4}{d_4 - d_2} \quad y_7 = \frac{d_4 y_3 - d_2 y_4}{d_4 - d_2}$$

$$x_8 = \frac{d_3 x_1 - d_1 x_4}{d_3 - d_1} \quad y_8 = \frac{d_3 y_1 - d_1 y_4}{d_3 - d_1}$$

Figure 34:
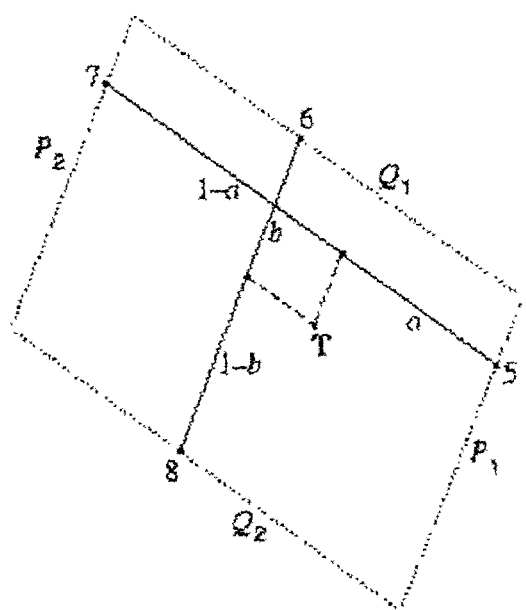
FIG. 34 illustrates the transformation of a grid cell into a parallelogram.

Now instead of being associated with a line segment, each of the two pairs of four grid parameters are associated with a pair of points, as shown in FIG. 34. If, for example, the target point lies on cell side 1-2, points 8 and 6 will coincide with 1 and 2 respectively, making Q dependent only on these two points, as required. If P and Q are expressed in terms of the coefficients a and b, using these equations:

$$P = (1-a)P_1 + aP_2 \quad Q = (1-b)Q_1 + bQ_2 \tag{5}$$

then standard bilinear interpolation leads to the following expressions for these coefficients:

$$a = \frac{(x_8 - x_6)(y - y_5) - (x - x_5)(y_8 - y_6)}{(x_8 - x_6)(y_7 - y_5) - (x_7 - x_5)(y_8 - y_6)} \tag{6}$$

$$b = \frac{(x - x_6)(y_7 - y_5) - (x_7 - x_5)(y - y_6)}{(x_8 - x_6)(y_7 - y_5) - (x_7 - x_5)(y_8 - y_6)}$$

Using this procedure, the grid cell has effectively been transformed from an arbitrary quadrangle to a parallelepiped (outlined with dashed lines in FIG. 34), although the shape of this parallelogram depends on the coordinates of the target point.

Figure 35:
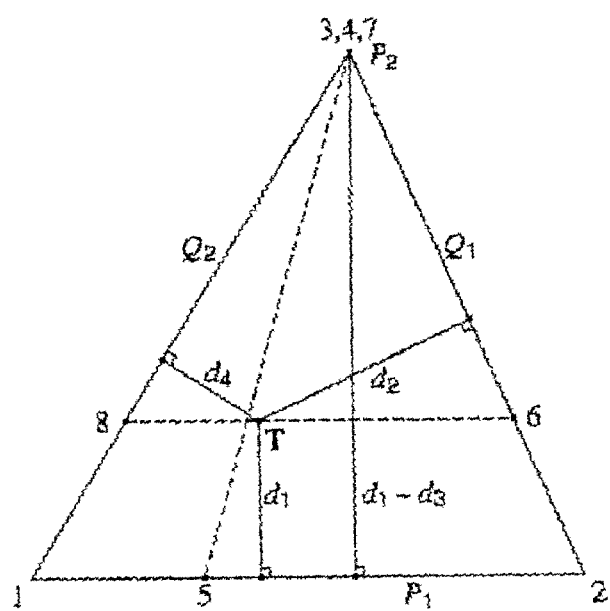
FIG. 35 illustrates the point and segment definitions for a triangular cell.

The simple method also could not accommodate cases when two adjacent corners of a grid cell coincided, as shown in FIG. 35. This can be a serious impediment since grids with triangular cells appear to be quite common. Often, this type of measurement grid arises when the "air" point (zero conductivity for magnetic grids or a relative permittivity of one for dielectric grids) is included in the grid, so that the sensor response does not change with "lift-off" and the entire edge of the grid folds into a single point. This air point can be used as a reference for sensor calibration, necessitating its inclusion in the grids to avoid the need for special treatment.

As a working example consider the case where points 3 and 4 coincide, as shown in FIG. 35. The main problem with applying the method outlined in the previous section directly is that the distance $d_3$ is not well defined, because points 3 and 4 do not uniquely define a line. It is not possible simply to use the distance between the target point T and point 3, because the polarity information is lost in this case (among other things) and the results would be wrong, especially if the target is outside the cell, which we hope to handle with at least some grace. The solution is to take the direction of the line through 3 and 4 to be parallel to the line through 1 and 2. A consequence of this is that the line through 6 and 8 will always be parallel to 1-2 and will pass through the target point T. The undefined distances need to be redefined via the segments as shown in FIG. 35.

Another special consideration is the cases when a grid folds in on itself. This look-up algorithm attempts to handle this kind of grid, at least in the simplest cases when there is no more than one "fold" or "twist". The main difficulty is that the searching stage of the algorithm may become confused near the fold line. For example, at the fold many grid cells are quadrangles whose opposite edges cross. It is not possible to determine whether the target point is "left" or "right" of a cell whose left and right edges intersect. In fact, it is not possible to decide whether the target point falls inside the cell at all. The approach taken in such cases is to try four different runs of the search algorithm described above, starting at the four corners of the grid. It has been found that this approach is quite effective at handling most cases, providing even for the possibility of finding two solutions in the areas where the grid surface overlaps itself. No attempt is made to determine which one of the two solutions is to be considered the "correct" one, as such decisions need to be made at a higher level, using other information.

Fast computation methods also facilitate the real-time estimate of material or geometric properties. These methods formulate the physical and mathematical models that separate the computations of intermediate results that depend on sensor geometry from those that depend upon the properties of the material under test. This allows the calculation of measurement grids or the running of parameter estimation routines based on minimization algorithms to be much more efficient. More specifically, in a typical calculation of the sensor response, intermediate calculations based solely on sensor geometry only need to be calculated once and not many times. These results can be stored and recalled as necessary, which can be much faster than the actual computation of the intermediate results and can provide dramatic decreases in processing times for iterative calculations. Iterative calculations are performed over a range of material or geometric properties during measurement grid generation and when minimizing the error between measurement and simulation data in parameter estimation routines.

The inventions described here relate to methods and apparatus for the nondestructive measurements of materials using sensors that apply electromagnetic fields to a test material and detect changes in the electromagnetic fields due to the proximity and properties of the test material. Although the discussion focused on magnetoquasistatic sensors, many of the concepts extend directly to electroquasistatic sensors as well.

While the inventions has been particularly shown and described with reference to preferred embodiments thereof, it will be understood to those skilled in the art that various changes in form and details may be made therein without departing from the spirit and scope of the invention as defined by the appended claims.

References incorporated herein by reference in their entirety:

Goldfine, N. G. (1990) "Uncalibrated, Absolute Property Estimation and Measurement Optimization for Conducting and Magnetic Media Using Imposed w-k Magnetometry," Ph.D.thesis, Department of Mechanical Engineering, Massachusetts Institute of Technology.

Goldfine, N. G. (1993) "Magnetometers for Improved Characterization in Aerospace Applications," Materials Evaluation, 51 (3).

Hood, R., L. M. Falicov, (1993) "Theory of the negative magnetoresistance in magnetic metallic multilayers," MRS Symposium Proceedings vol. 313.

Press, W. H., B. P. Flannery, S. A. Teukolsky, W. T. Vetterling (1992) "Numerical Recipes; The Art of Scientific Computing."

Rempt, R., (2001) presented at the 2001 Aeromat Conference, Jun. 11–14, 2001.

Wincheski, B., J. Simpson, M. Namkung, D. Perey, E. Scales, and R. Louie (2001) presented at the 2001 QNDE Conference, New Brunswick, Me.

The following documents are also incorporated herein by reference in their entirety.

1. NASA Phase I Proposal Titled "Shaped Field Giant Magnetoresistive Sensor Arrays for Material Testing", Topic #A1.05-8767, dated Jun. 5, 2001.
2. Technical Paper titled "Flexible Eddy Current Sensors and Scanning Arrays for Inspection of Steel and Alloy Components", presented at the $7^{th}$ EPRI Steam Turbine/Generator Workshop and Vendor Exposition, Aug. 20–23, 2001.
3. Technical Paper titled "High-Resolution Eddy Current Sensor Arrays for Detection of Hidden Damage including Corrosion and Fatigue Cracks", presented at the NASA/FAA/DoD Conference on Aging Aircraft, Sep. 10–13, 2001.
4. Presentation Slides titled "High-Resolution Eddy Current Sensor Arrays with Inductive and Magnetoresistive Sensing Elements", presented at the ASNT Fall Conference, Oct. 15–19, 2001.
5. Massachusetts Institute of Technology Doctoral Thesis (2001), titled "Deep Penetration Magnetoquasistatic Sensors," by Yanko Sheiretov.

What is claimed is:

1. A test circuit comprising:
   a primary winding which imposes two or more dominant spatial periods of a magnetic field into a test substrate when driven by electric current, the primary winding comprising two or more coils with different current distributions, the relative current directions in the coils being switched to provide a different dominant spatial period, with current simultaneously passing through said coils; and
   at least one sensing element which senses the response of the test substrate to the imposed magnetic field.

2. A test circuit comprising:
   a primary winding which imposes two or more dominant spatial periods of a magnetic field into a test substrate when driven by electric current, the primary winding comprising two or more discrete concentric loops, the relative current direction in the loops being switched to provide a different dominant spatial period, where the current distribution approximates a first order Bessel function envelope;

at least one sensing element which senses the response of the test substrate to the imposed magnetic field.

3. A test circuit comprising:

a primary winding which imposes two or more dominant spatial periods of a magnetic field into a test substrate when driven by electric current, the primary winding lacking a net dipole moment and comprising two or more coils with different current distributions, the relative current directions in the coils being switched to provide a different dominant spatial period; and at least one sensing element which senses the response of the test substrate to the imposed magnetic field.

4. A test circuit as claimed in claim 3 where the current through the coils of the primary winding approximate a sinusoidal distribution and additional current carrying segments near the ends of the primary winding reduce the dipole moment.

5. A test circuit comprising:

a primary winding which imposes two or more dominant spatial periods of a magnetic field into a test substrate when driven by electric current, the primary winding comprising two or more coils with different current distributions, the relative current directions in the coils being switched to provide a different dominant spatial period; and at least one sensing element which senses the response of the test substrate to the imposed magnetic field, where the at least one sensing element contains a giant magnetoresistive sensor, the sensor being biased by a DC magnetic field in the vicinity of the sensor.

6. A test circuit as claimed in claim 5 where DC the magnetic field is created by an electric current through a coil encircling the giant magnetoresistive sensor.

7. A test circuit as claimed in claim 1 where at least one sensing element contains a SQUID sensor.

8. A test circuit as claimed in claim 1 where at least one sensing element contains a Hall effect sensor.

9. A test circuit comprising:

a primary winding which imposes two or more dominant spatial periods of a magnetic field into a test substrate when driven by electric current, the primary winding comprising two or more coils with different current distributions, the relative current directions in the coils being switched to provide a different dominant spatial period, where the primary winding contains substantially parallel segments and a linear array of sensing elements containing giant magnetoresistive sensors placed between two adjacent parallel segments; and at least one sensing element which senses the response of the test substrate to the imposed magnetic field.

10. A test circuit as claimed in claim 9 further comprising a second linear array of sensing elements placed parallel to the first array and offset by half a sensing element dimension parallel to the array direction.

11. A test circuit as claimed in claim 1 where the primary winding contains substantially parallel segments and a two-dimensional array of sensing elements that spans the footprint of the primary winding.

12. A test circuit comprising:

a primary winding which imposes two or more dominant spatial periods of a magnetic field into a test substrate when driven by electric current, the primary winding comprising two or more coils with different current distributions, the relative current directions in the coils being switched to provide a different dominant spatial period, where the primary winding contains substantially parallel segments and a two-dimensional array of sensing elements that spans the footprint of the primary winding; and at least one sensing element which senses the response of the test substrate to the imposed magnetic field, where the at least one sensing element uses a giant magnetoresistive sensor.

13. A test circuit comprising:

a primary winding which imposes two or more dominant spatial periods of a magnetic field into a test substrate when driven by electric current, the primary winding comprising two or more coils with different current distributions, the relative current directions in the coils being switched to provide a different dominant spatial period, where the primary winding contains concentric segments and an array of sensing elements that spans the circumference of one of the primary winding segments; and at least one sensing element which senses the response of the test substrate to the imposed magnetic field.

14. A test circuit as claimed in claim 13 where at least one sensing element uses a giant magnetoresistive sensor.

15. A test circuit comprising:

a primary winding which imposes two or more dominant spatial periods of a magnetic field into a test substrate when driven by electric current, the primary winding comprising two or more coils with different current distributions, the relative current directions in the coils being switched to provide a different dominant spatial period; and at least one sensing element which senses the response of the test substrate to the imposed magnetic field, where the test substrate contains a magnetizable foam layer having a known thickness.

16. A test circuit as claimed in claim 1 where the coils are rectangular loops.

17. A test circuit comprising:

a means for imposing two or more dominant spatial periods of a magnetic field into a test substrate when driven by electric current, the means including a means for simultaneously applying current to at least two conducting segments for creating the magnetic field when driven by said current and a means for switching the relative current direction in a segment to provide a different dominant spatial period; and a means for sensing the response of the test substrate to the imposed magnetic field.

18. A test circuit as claimed in claim 17 where the conducting segments are linear.

19. A test circuit comprising:

a primary winding which imposes two or more dominant spatial periods of a magnetic field into a test substrate when driven by electric current, the primary winding comprising two or more coils with different current distributions, the relative current directions in the coils being switched to provide a different dominant spatial period, where the primary winding comprises at least two concentric loops; and at least one sensing element which senses the response of the test substrate to the imposed magnetic field.

20. A test circuit as claimed in claim 19 where the current distribution approximates a first order Bessel function envelope.

* * * * *